United States Patent
Kenez et al.

(10) Patent No.: US 9,926,332 B2
(45) Date of Patent: Mar. 27, 2018

(54) DIHYDRO-OXAZINOBENZODIAZEPINE COMPOUNDS, A PROCESS FOR THEIR PREPARATION AND PHARMACEUTICAL COMPOSITIONS CONTAINING THEM

(71) Applicant: Egis Gyogyszergyar Zrt., Budapest (HU)

(72) Inventors: Agnes Kenez, Gegeny (HU); Ferenc Bertha, Budapest (HU); Jozsef Barkoczy, Budapest (HU); Ferenc Antoni, Budapest (HU); Istvan Gacsalyi, Budapest (HU); Balazs Mihalik, Budapest (HU); Gabor Gigler, Budapest (HU); Krisztina Moricz, Budapest (HU); Gabor Nemeth, Budapest (HU); Agnes Angyalne Pataki, Budapest (HU); Gabor Laszlo Kapus, Pecel (HU); Adrienn Palvolgyi, Oroszlany (HU); Istvan Ling, Budapest (HU); Janos Petho, Budapest (HU); Gyula Simig, Budapest (HU); Balazs Volk, Budapest (JE); Lax Gyorgyi Kovanyine, Budapest (HU); Andras Dancso, Budapest (HU)

(73) Assignee: Egis Gyogyszergyar Zrt., Budapest (HU)

( * ) Notice: Subject to any disclaimer, the term of this patent is extended or adjusted under 35 U.S.C. 154(b) by 0 days.

(21) Appl. No.: 15/113,083

(22) PCT Filed: Jan. 20, 2015

(86) PCT No.: PCT/HU2015/000003
§ 371 (c)(1),
(2) Date: Jul. 21, 2016

(87) PCT Pub. No.: WO2015/110848
PCT Pub. Date: Jul. 30, 2015

(65) Prior Publication Data
US 2017/0002020 A1 Jan. 5, 2017

(30) Foreign Application Priority Data
Jan. 21, 2014 (HU) .................................. 1400025

(51) Int. Cl.
*A61K 31/551* (2006.01)
*C07D 498/04* (2006.01)
*C07D 265/36* (2006.01)
*C07D 413/06* (2006.01)

(52) U.S. Cl.
CPC ......... *C07D 498/04* (2013.01); *C07D 265/36* (2013.01); *C07D 413/06* (2013.01)

(58) Field of Classification Search
CPC .......................... A61K 31/551; C07D 498/04
USPC .......................................... 514/220; 540/557
See application file for complete search history.

(56) References Cited

U.S. PATENT DOCUMENTS

| 8,778,932 B2 | 7/2014 | Ling et al. |
| 2012/0232065 A1 | 9/2012 | Ling et al. |

FOREIGN PATENT DOCUMENTS

| EP | 0171702 A1 | 2/1986 |
| WO | 2012/120206 A1 | 9/2012 |

OTHER PUBLICATIONS

International Search Report dated May 7, 2015 issued in corresponding PCT/HU2015/000003 application (4 pages).
Written Opinion of the International Searching Authority dated May 7, 2015 issued in corresponding PCT/HU2015/000003 application (5 pages).
Database Registry [Online] Chemical Abstracts Service, Apr. 15, 2012 XP002738455.
Database Registry [Online] Chemical Abstracts Service, Apr. 15, 2012 XP002738456.
Database Registry [Online] Chemical Abstracts Service, Jan. 16, 2014 XP002738457.

*Primary Examiner* — Brenda L Coleman
(74) *Attorney, Agent, or Firm* — Millen White Zelano and Branigan, PC; Csaba Henter

(57) ABSTRACT

Compounds of formula (I)

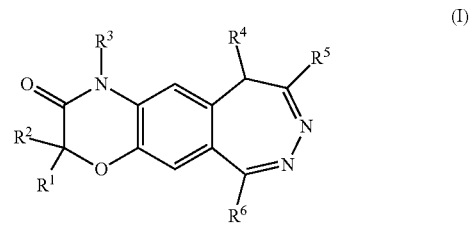

having a selective dual action on the central GABAergic system, and a process for their preparation and to pharmaceutical compositions containing them.

20 Claims, 2 Drawing Sheets

DIHYDRO-OXAZINOBENZODIAZEPINE COMPOUNDS, A PROCESS FOR THEIR PREPARATION AND PHARMACEUTICAL COMPOSITIONS CONTAINING THEM

TECHNICAL FIELD

The present invention relates to new 1,10-dihydro[1,4]oxazino[3,2-h][2,3]benzodiazepin-2(3H)-one compounds having a selective dual action on the central GABAergic system, to a process for their preparation and to pharmaceutical compositions containing them.

BACKGROUND ART

γ-Aminobutyric acid (or GABA) is the predominant inhibitory neurotransmitter in the mammalian central nervous system. In the prosencephalon, GABA is mainly synthesised by interneurons which co-ordinate complex neuronal circuits via $GABA_A$ and $GABA_B$ receptors. The $GABA_A$ receptors are ligand-activated chloride channels largely localised to the plasma membrane. Typically, $GABA_A$ receptors are made up of five analogous membrane spanning protein subunits that assemble from a reportory of protein subunits α (6 genes): β (3 genes): γ (3 genes) in a ratio of 2:2:1, respectively. It is generally assumed that two identical isoforms of each subunit are incorporated into a particular receptor [Atack J R (2011) Curr Top Med Chem 11: 1203-1214].

Classical benzodiazepine compounds such as diazepam allosterically modulate $GABA_A$ receptors by binding to the benzodiazepine (BDZ) site that spans the interface of one of the alpha and the gamma subunit of the receptor. Diazepam as a non-selective positive allosteric modulator (PAM) of GABA action brings about sedative, hypnotic, anxiolytic, anti-convulsant, amnesic, anti-nociceptive and myorelaxant effects.

Knock-in genetic experiments have shown that the $α_1$ subunit is responsible for the sedative actions whilst the $α_2$ and possibly $α_3$ subunits are responsible for the anxiolytic potency of BDZ-site PAMs [Möhler H (2012) Neuropharmacol 62: 42-53]. Compounds behaving as negative allosteric modulators (NAM) at the BDZ-site are also referred to as "inverse agonists". BDZ-site NAM compounds that have no $GABA_A$ isoform selectivity show nootropic properties in preclinical tests. However, major pro-convulsive and anxiogenic effects have prevented further clinical studies from being carried out on these compounds The biological functions of $GABA_A$ receptors containing the $α_5$ subunit have been assessed in genetically altered animals as well as with the aid of BDZ-site modulators that appear to be selective in vitro. Electrophysiological studies show that a tonic inhibitory potential exists in most neocortical pyramidal neurons, and that this potential sets the intrinsic excitability threshold of the cells. Moreover, in prefrontal cortex pyramidal cells but not in hippocampal CA1 pyramidal cells, there is a complementarity between $I_h$ mediated by HCN channels and the $GABA_A$ $α_5$ mediated tonic current in regulating neuronal firing. This suggests that $GABA_A$ $α_5$ inhibitors will have a much greater impact on pyramidal cell activity in the frontal cortex than in the hippocampus. Behaviourally, gene-deletion or reduction of the number of $GABA_A$ $α_5$ receptors is associated with an improvement in cognitive functions. Moreover, treatment with various $α_5$ selective NAMs enhanced cognitive performance in intact rodents as well as in a mouse model of Down's syndrome. In humans, the amnestic effect of acute alcohol consumption was attenuated by an $α_5$ selective BDZ-site NAM.

GABAergic neurotransmission is also fundamentally important for the normal function of the dorsolateral prefrontal cortex. It has been proposed that deficits in working memory in schizophrenic patients might be a consequence of reduced GABAergic control of neural circuits in the dorsolateral prefrontal cortex [Lewis D A et al. (2008) Am. J. Psychiatry. 165: 1585-1593]. At the cellular level, GABAergic chandelier cells regulate the activity of pyramidal neurons via $GABA_A$ $α_2$ receptors located at the axon initial segment. This mechanism appears important for the maintenance the optimal synchronization of pyramidal neuron activity at gamma band frequency in the prefrontal cortex. However, a recent report indicated that enhancement of $GABA_A$ $α_2/α_3$ function may not be sufficient for the improvement of cognitive function [Buchanan R W et al. (2011) Biol. Psych. 69: 442-449]. Indeed, prevailing theories stress the need for hippocampal-prefrontal synchronisation and connectivity for optimal cognitive function [Akbarian S (2008) Am. J. of Psychiatry 165: 1507-1509; Uhlhaas P J et al (2008) Schizophr Bull 34: 927-943].

On the basis of the mechanisms outlined above, simultaneous augmention of GABAergic neurotransmission at $GABA_A$ $α_2$ subunits on the axon initial segments of pyramidal cells and attenuation of tonic inhibition by blockade of $GABA_A$ $α_5$ receptors in the hippocampus may be predicted to improve the cognitive dysfunction in different disorders such as Alzheimer's disease, Down's syndrome, schizophrenia, Huntington's disease, and dementias of different origin.

There exists a large, unsatisfied need in the treatment of cognitive deficits associated with various age-related disorders, neurodegenerative or vascular disorders as well as schizophrenia. Current treatments for Alzheimer's disease, the pathology with the greatest prevalence, are based either on inhibition of cholinesterase (e.g. donepezil) or on NMDA antagonism (memantine). However, cholinesterase inhibitors have a large number of undesirable effects relating to their mechanism of action, whilst the true efficacy of memantine is limited. Consequently, having new therapies of greater efficacy and better tolerability would be especially valuable.

International patent application WO 2012120206 discloses a family of compounds having the following structure:

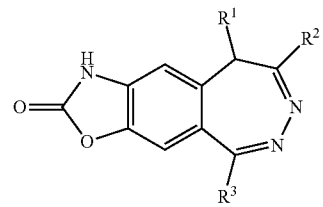

These compounds are disclosed to be useful in the treatment or prevention of psychiatric and neurological disorders, as selective ligands for the $α_5$ subunit of the $GABA_A$ receptor.

DISCLOSURE OF THE PRESENT INVENTION

The compounds of the present invention are new and have especially valuable properties as a result of their simultaneous activity on $GABA_A$ receptors containing the $α_2$ and $α_5$ subunits. The specific therapeutical advantage of the compounds of the present invention is the selective dual action on the central GABAergic system.

The present invention relates to compounds of formula (I):

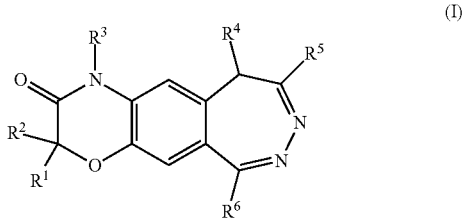

wherein
$R^1$, $R^2$ are independently selected from hydrogen and $C_{1-4}$ alkyl;
$R^3$ is hydrogen or $C_{1-4}$ alkyl group which is unsubstituted or substituted by phenyl, pyridyl, or amino optionally substituted by $C_{1-4}$ alkyl;
$R^4$ is hydrogen;
$R^5$ is $C_{1-4}$ alkyl group;
$R^6$ is selected from monocyclic aryl, which is a six membered ring unsubstituted or substituted by one or more identical or different groups selected from $C_{1-4}$ alkyl groups, $C_{1-4}$ alkoxy, $C_{1-4}$ halogenalkyl, phenyl, phenoxy, halogen, nitro; or mono- or bi- or tricyclic heteroaryl group consisting of five or six membered ring(s) having 1 to 3 identical or different hetero atoms selected from nitrogen, oxygen and sulfur, in which at least one of the rings is aromatic, and wherein the rings are optionally substituted by one or more identical or different groups selected from $C_{1-4}$ alkyl, mono-, di-, tri-halogenated $C_{1-4}$ alkyl, $C_{1-4}$ alkoxy, hydroxyl, halogen, their positional isomers, their racemates and enantiomers, their diastereoisomers, and also their addition salts with a pharmaceutically acceptable acid, their solvates, their complexes, adducts and prodrugs.

Among the pharmaceutically acceptable acids there may be mentioned without implying any limitation, hydrochloric acid, hydrobromic acid, sulfuric acid, acetic acid, trifluoroacetic acid, lactic acid, malonic acid, succinic acid, glutamic acid, fumaric acid, maleic acid, phosphoric acid, citric acid, oxalic acid, methanesulfonic acid, benzenesulfonic acid, para-toluenesulfonic acid, camphoric acid, etc.

Unsubstituted or substituted mono- bi-, tricyclic heteroaryl groups consist of five or six membered ring(s) having one to three heteroatom(s) selected from oxygen nitrogen and sulphur, wherein in the bi-, tricyclic group at least one ring is condensed with said heterocyclic ring.

For example monocyclic heteroaryl group is phenyl substituted tiophene and bicyclic heteroaryl groups are quinolone, indole, oxazole, benzothiophene, benzofuran and tricyclic heteroaryl group are naphto-thiophene, dibenzothiophene, naphtofuran, benzobifuran.

Preferable representatives of the compound of formula (I) according to the present invention are those wherein $R^1$, $R^2$ is propyl, ethyl, methyl or hydrogen, $R^3$ is hydrogen, methyl, ethyl, or benzyl and $R^5$ is from methyl or ethyl.

Further preferable representatives of the compound of formula (I) according to the present invention are those wherein $R^1$, $R^2$ is methyl or hydrogen, $R^3$ is hydrogen and $R^5$ is methyl.

The present invention relates to the compound of formula (I), wherein $R^6$ is phenyl substituted by one or more halogen or $C_{1-4}$ alkyl which is substituted by one or more halogen. Further, according to the present invention the compounds of formula (I) are preferred wherein $R^6$ is phenyl substituted by one or more fluoro or trifluoromethyl. According to a further aspect of the present invention, there are provided compounds of formula (I), wherein $R^6$ is a benzofuranyl or a benzothienyl group wherein the rings are optionally substituted by one or more identical or different groups selected from $C_{1-4}$ alkyl, $C_{1-4}$ haloalkyl, $C_{1-4}$ alkoxy, halogen, hydroxyl.

In the present specification, $C_{1-4}$ alkyl means a saturated linear or branched hydrocarbon chain or cyclic hydrocarbon ring. $C_{1-4}$ haloalkyl means a $C_{1-4}$ alkyl as defined above substituted by one or more identical or different halogen atom(s) which are preferably selected from F, Cl. Generally halogen atoms mean F, Cl, Br, I.

Another preferable group of the compound of formula (I) are wherein $R^1$, $R^2$ is propyl, ethyl, methyl or hydrogen, $R^3$ is hydrogen, methyl, ethyl or benzyl, $R^5$ is methyl or ethyl and $R^6$ is 1-benzofuran-2-yl or 1-benzothiophen-2-yl group which is substituted by one to three identical or different groups which are independently selected from $C_{1-4}$ alkyl, $C_{1-4}$ alkoxy, halogen, hydroxyl.

Still further preferable group of the compound of formula (I) are wherein $R^6$ is 1-benzofuran-2-yl or 1-benzothiophen-2-yl group which is substituted by one to three identical or different groups which is independently selected from methyl, ethyl, methoxy, fluoro, chloro and hydroxyl.

Still further preferable group of the compound of formula (I) are wherein $R^6$ represents a 1-benzofuran-2-yl group, substituted in position 3 by ethyl or methyl and in any of positions 4 to 7 by one or two identical or different group(s) independently selected from ethyl, chloro, methoxy, and hydroxyl.

Still further preferable group of the compound of formula (I) are wherein $R^6$ represents a 1-benzofuran-2-yl group, substituted in position 3 by ethyl or methyl and in any of positions 4 to 7 by one or two identical or different group(s) independently selected from ethyl, chloro, methoxy, and hydroxyl.

Still further preferable group of the compound of formula (I) are wherein $R^6$ represents 1-benzothien-2-yl group, substituted in position 3 by ethyl or methyl and in any of positions 4 to 7 by one or two identical or different group(s) independently selected from chloro and fluoro. Further, according to the present invention the compound of formula (I), are preferred wherein $R^1$, $R^2$ is methyl or hydrogen; $R^4$, $R^3$ is hydrogen, $R^5$ is methyl and $R^6$ is 1-benzofuran-2-yl or 1-benzothiophen-2-yl group which are substituted by one to three identical or different groups which are independently selected from methyl, ethyl, methoxy, fluoro, chloro, and hydroxyl. According to the present invention, the most preferred compounds of formula (I) are wherein $R^1$, $R^2$ is methyl or hydrogen; $R^4$, $R^3$ is hydrogen, $R^5$ is methyl and $R^6$ represents 1-benzofuran-2-yl group, substituted in position 3 by ethyl or methyl and in any of positions 4 to 7 by one or two identical or different group(s) independently selected from ethyl, chloro, methoxy, and hydroxyl. According to the present invention, especially preferred compounds of formula (I) are wherein $R^1$, $R^2$ is methyl or hydrogen $R^4$, $R^3$ is hydrogen, $R^5$ is methyl and $R^6$ represents 1-benzothien-2-yl group, substituted in position 3 by ethyl or methyl and in any of positions 4 to 7 by one or two identical or different group(s) independently selected from chloro and fluoro.

The most preferred compounds of the invention are:

6-(4-fluoro-3-methyl-1-benzothiophen-2-yl)-3,9-dimethyl-1,10-dihydro[1,4]oxazino[3,2-h][2,3]benzodiazepin-2(3H)-one

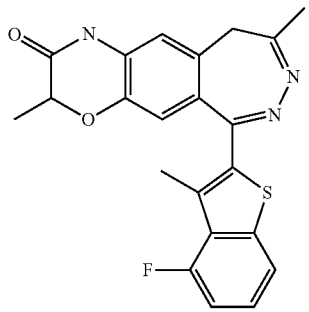 [SMILES: CC1=NN=C(c2sc3cccc(F)c3c2C)c2cc3c(cc2C1)NC(=O)C(C)O3]

6-(5-methoxy-3-methyl-1-benzofuran-2-yl)-3,9-dimethyl-1,10-dihydro[1,4]oxazino[3,2-h][2,3]benzodiazepin-2(3H)-one

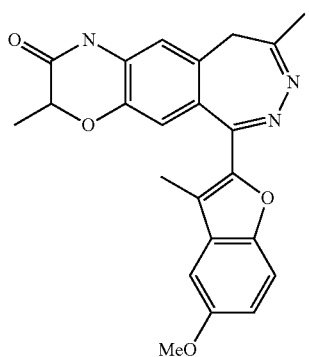 [SMILES: COc1ccc2oc(C3=NN=C(C)Cc4cc5c(cc43)OC(C)C(=O)N5)c(C)c2c1]

6-(6-chloro-3-methyl-1-benzothiophen-2-yl)-3,9-dimethyl-1,10-dihydro[1,4]oxazino[3,2-h][2,3]benzodiazepin-2(3H)-one

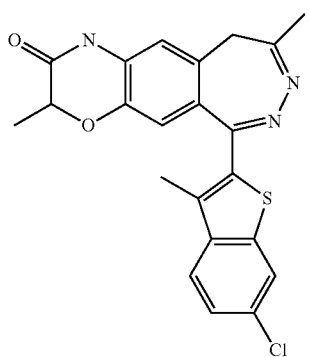 [SMILES: CC1=NN=C(c2sc3cc(Cl)ccc3c2C)c2cc3c(cc2C1)NC(=O)C(C)O3]

6-(6-chloro-5-fluoro-3-methyl-1-benzothiophen-2-yl)-3,9-dimethyl-1,10-dihydro[1,4]oxazino[3,2-h][2,3]benzodiazepin-2(3H)-one

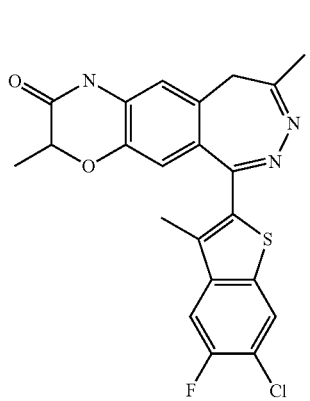 [SMILES: CC1=NN=C(c2sc3cc(Cl)c(F)cc3c2C)c2cc3c(cc2C1)NC(=O)C(C)O3]

6-(5-chloro-3-ethyl-1-benzothiophen-2-yl)-3,9-dimethyl-1,10-dihydro[1,4]oxazino[3,2-h][2,3]benzodiazepin-2(3H)-one

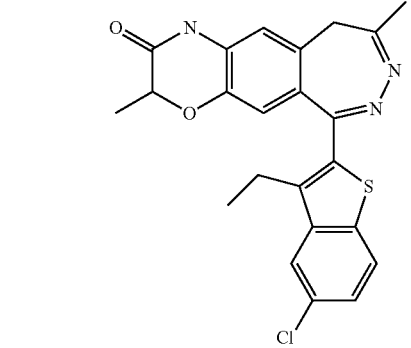 [SMILES: CCc1c(C2=NN=C(C)Cc3cc4c(cc32)OC(C)C(=O)N4)sc2ccc(Cl)cc12]

6-(5-chloro-3-methyl-1-benzofuran-2-yl)-3,9-dimethyl-1,10-dihydro[1,4]oxazino[3,2-h][2,3]benzodiazepin-2(3H)-one

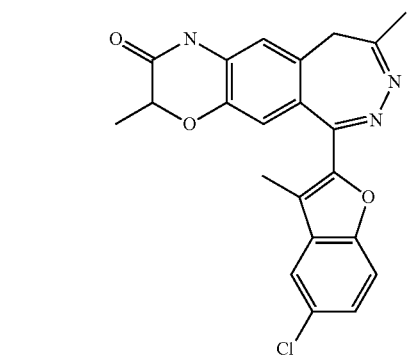 [SMILES: CC1=NN=C(c2oc3ccc(Cl)cc3c2C)c2cc3c(cc2C1)NC(=O)C(C)O3]

6-(3,5-diethyl-1-benzofuran-2-yl)-3,9-dimethyl-1,
10-dihydro[1,4]oxazino[3,2-h][2,3]benzodiazepin-2
(3H)-one

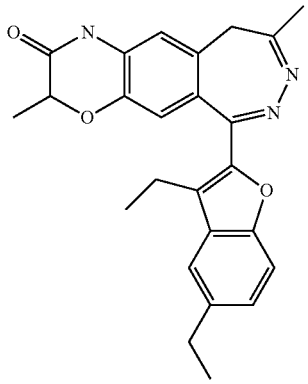 [SMILES: CCc1ccc2oc(C3=NN=C(C)Cc4cc5c(cc43)OC(C)C(=O)N5)c(CC)c2c1]

6-(5-hydroxy-3-methyl-1-benzofuran-2-yl)-3,9-dimethyl-1,10-dihydro[1,4]oxazino[3,2-h][2,3]benzodiazepin-2(3H)-one

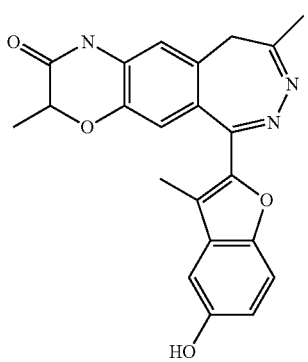 [SMILES: CC1=NN=C(c2oc3ccc(O)cc3c2C)c2cc3c(cc2C1)NC(=O)C(C)O3]

Positional isomers, enantiomers, diastereoisomers, addition salts formed with a pharmaceutically acceptable acid and also solvates, complexes and adducts of compounds of formula (I) form an integral part of the invention.

Pure enantiomers of the racemic compounds of formula (I) can be obtained using chiral HPLC chromatographic separation of the racemate, by resolution of the racemate via the diastereomeric derivatives, or by chiral synthesis. The enantiomers thus obtained were characterized also with optical rotation measurement.

The invention also relates to a process for the preparation of compounds of formula (I),
comprising the treatment of compound of formula (II)

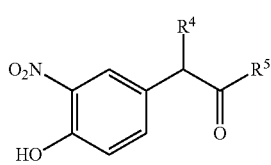
(II)

wherein $R^4$ is hydrogen and $R^5$ represents a linear or branched $C_{1-4}$ alkyl group;

with a compound of formula (III)

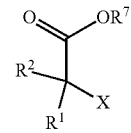
(III)

wherein $R^1$ and $R^2$ are independently selected from hydrogen or a linear or branched $C_{1-4}$ alkyl;

$R^7$ represents linear or branched $C_{1-4}$ alkyl group, X represents a leaving group, preferably Cl or Br, to yield compound of formula (IV);

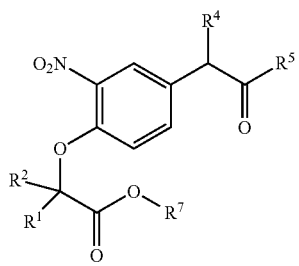
(IV)

wherein $R^1$, $R^2$, $R^4$, $R^5$ and $R^7$ are as defined for formula (I) and (III);

which is reduced and optionally N-alkylating to yield the compound of formula (V),

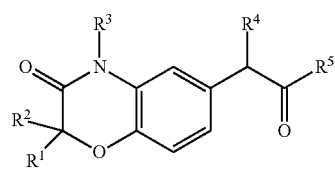
(V)

wherein $R^1$, $R^2$, $R^3$, $R^4$ and $R^5$ are as defined for formula (I);

brominating to give the compound of formula (V) to give compound (VI),

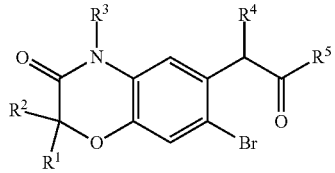
(VI)

wherein $R^1$, $R^2$, $R^3$, $R^4$ and $R^5$ are as defined for formula (I);

converting the compound of formula (VI), by treatment with at least one alcohol or diol into compound (VII)

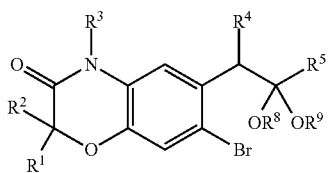
(VII)

wherein $R^1$, $R^2$, $R^3$, $R^4$ and $R^5$ are as defined for formula (I), wherein $R^8$ and $R^9$ each represents a $C_{1-4}$ alkyl group, or $R^8$ and $R^9$ together form $C_{2-6}$ alkylene;
converting the thus obtained product by exchanging the bromo atom for an alkali or magnesium atom and by reacting the thus-obtained alkali or magnesium compound with an approximately equimolar amount of a carboxylic acid derivative of the general formula (VIII) to give compound (IX)

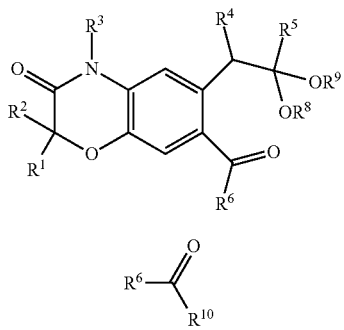
(IX)

(VIII)

wherein $R^1$, $R^2$, $R^3$, $R^4$, $R^4$ and $R^6$ are as defined for formula (I), $R^8$ and $R^9$ are as defined for formula (VII) an $R^{10}$ represents Cl, or Br, or $OR^{11}$ [wherein $R^{11}$ represents a $(C_1-C_4)$ alkyl group], or $NR^{12}R^{13}$ [wherein $R^{12}$ and $R^{13}$ each denotes a $(C_1-C_4)$ alkyl or a methoxy group];

Method for transforming the compound of the formula (IX) in the compound of the formula (I) which comprises
a) treating the compound (IX) with an acid followed by cyclisation with hydrazine or hydrazine hydrate in one pot to produce compound formula (I), or
b) converting the compound (IX) by acidic treatment to compound (X)

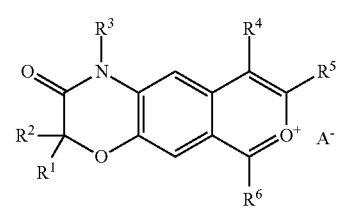
(X)

wherein $R^1$, $R^2$, $R^3$, $R^4$, $R^4$ and $R^6$ are as defined for formula (I) and $A^-$ is an anion;
and reacting the thus obtained compound of the formula (X) with hydrazine or hydrazine hydrate to produce compound of formula (I), or
c) converting the compound (IX) by acidic treatment to compound (XI)

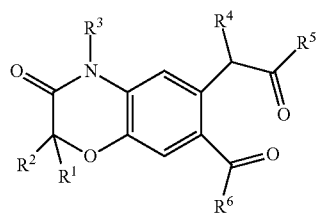
(XI)

wherein $R^1$, $R^2$, $R^3$, $R^4$, $R^5$ and $R^6$ are as defined for formula (I)
reacting the compound of formula (XI) with hydrazine or hydrazine hydrate to produce compound of formula (I).

A process for the preparation of compounds of formula (I), comprising the reduction of compound of formula (V) to alcohol of formula (XII)

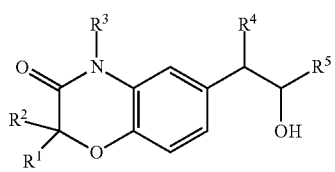
(XII)

wherein
$R^1$, $R^2$, $R^3$, $R^4$ and $R^5$ are as defined for formula (I);
reacting the thus obtained product, with an aldehyde of formula (XIII) under acidic conditions to afford the isochroman of the formula (XIV)

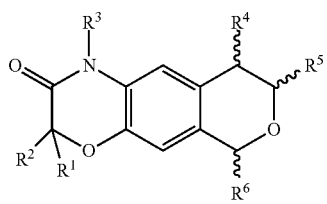
(XIV)

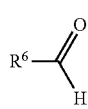
(XIII)

wherein $R^6$ are as defined for formula (I);

The compounds of formulae (II), (III) and (VIII) are commercially available or readily accessible to the person skilled in the art using conventional chemical reactions or chemical reactions described in the literature.

The compounds of the present invention are simultaneously active on $GABA_A$ receptors containing the $\alpha_2$ and $\alpha_5$ subunits. Augmentation of the effects of the neurotransmitter GABA in prefrontal cortex is accompanied by attenuation of GABA mediated tonic inhibition in the hippocampus. Such compounds are expected to be useful in the treatment or prevention of psychiatric and neurological disorders characterised by cognitive deficits, such as schizophrenia, unipolar depression, Alzheimer's disease, vascular dementia, autism spectrum disorders, Down's syndrome, fragile X syndrome, Parkinson's disease, Huntington's disease. Other possible therapeutic indications are related to various anxiety states such as generalised anxiety, panic disorder with or without agoraphobia, obsessive-compulsive disorders, post-traumatic stress disorders and bipolar disorders. The compounds of the invention may be used in the treatment of sequel of a cerebral vascular accident and sequelae of brain, spine or medullary trauma.

The compounds would preferably be used in the treatment or prevention of Alzheimer's disease, vascular dementia such as dementia due to the consequences of a cerebral vascular accident, Huntington's disease and Down's syndrome.

The invention relates also to pharmaceutical compositions comprising, as active ingredient, at least one compound of formula (I) on its own or in combination with one or more inert, non-toxic excipients or carriers. Among the pharmaceutical compositions according to the invention mention may be made especially of those that are suitable for oral, parenteral (intravenous or subcutaneous) or intranasal administration, tablets or dragées, sublingual tablets, capsules, lozenges, suppositories, creams, ointments, dermal gels, injectable preparations and drinkable suspensions.

The useful dosage varies according to the age and weight of the patient and the nature and severity of the disorder, and also the route of administration, which may be nasal, rectal, parenteral or oral. Generally, the unit dose ranges from 0.1 to 1000 mg per 24 hours for treatment in 1 to 3 administrations.

Figure 1:
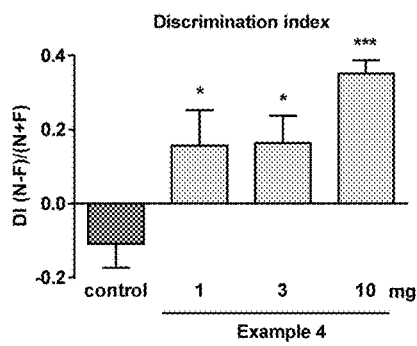
FIG. 1 and FIG. 2. Procognitive effects of the compounds of Example 4 and Example 24 in the object recognition model in mice after i.p. administration. Mean values±S.E.M. (n=8-11/group); Dunnett test following ANOVA (*:$p<0.05$, :$p<0.01$, *:$p<0.001$). Discrimination index: Duration of new object exploration (s)−Duration of familiar object exploration (s)/Duration of new object exploration (s)+ Duration of familiar object exploration (s).

The present invention will be illustrated with the following examples, but the present invention should not be construed to be limited thereto.

EXAMPLE 1

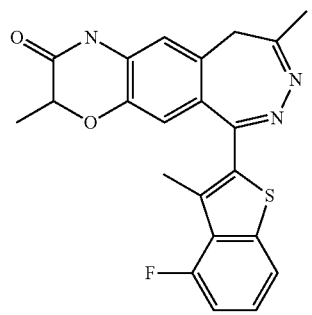

6-(4-fluoro-3-methyl-1-benzothiophen-2-yl)-3,9-dimethyl-1,10-dihydro[1,4]oxazino[3,2-h][2,3]benzodiazepin-2(3H)-one

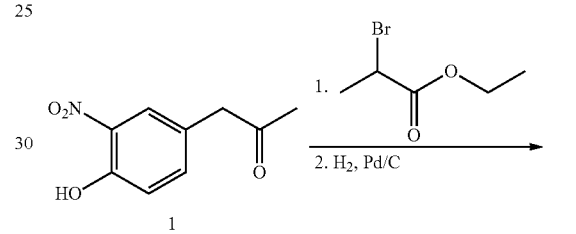

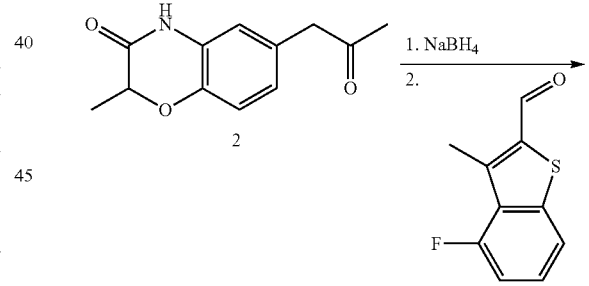

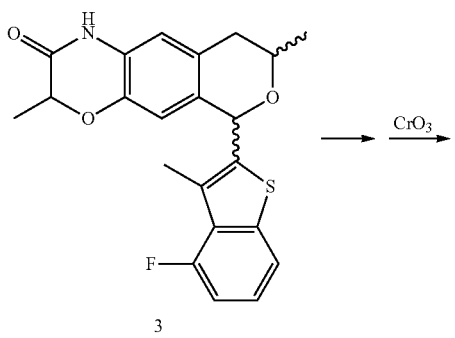

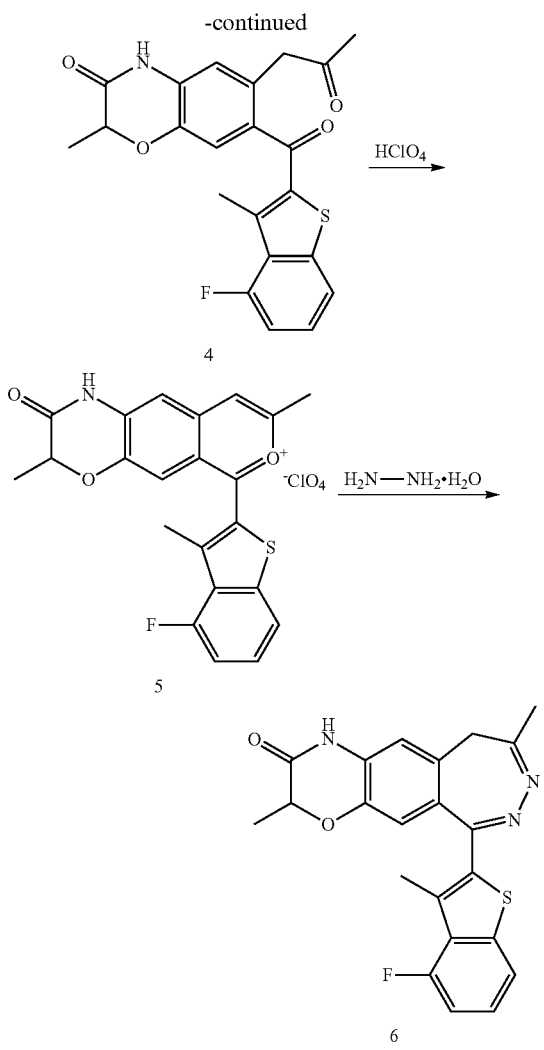

(1) The mixture of 1-(4-hydroxy-3-nitrophenyl)propan-2-one (1, 20.0 g, 102.5 mmol), ethyl 2-bromo-propanoate (14.4 mL, 110 mmol) and acetone (550 mL) was stirred, and $K_2CO_3$ (42.0 g, 303 mmol) was added and the mixture was refluxed for 7 hours. The precipitate was filtered, washed with acetone (3×100 mL), and evaporated. The oily residue (28.0 g, 94 mmol) was dissolved in acetic acid (200 mL), and Pd/C (10 w/w %, 8.0 g) was added. It was hydrogenated at room temperature at 10 bar pressure over a period of 8 hours. The catalyst was filtered, washed with acetic acid (3×25 mL). The acetic acid was evaporated and the solid residue was recrystallized from a mixture of DIPE and methanol to give 2-methyl-6-(2-oxopropyl)-2H-1,4-benzoxazin-3(4H)-one (2, 15.5 g, 69%), mp: 163-166° C.

(2) To the suspension of 2-methyl-6-(2-oxopropyl)-2H-1,4-benzoxazin-3(4H)-one (2, 10.0 g, 45.6 mmol) in methanol (100 mL) was added slowly sodium borohydride (1.82 g, 48.1 mmol) at 0° C., and the mixture was stirred for 30 minutes at 0° C. and for further 90 minutes at room temperature. Acetic acid (7.3 mL) was added, and the solvents were evaporated. Water (40 mL) was added to the residue and the crystalline product was filtered, washed with water (3×15 mL) and dried to give 6-(2-hydroxypropyl)-2H-1,4-benzoxazin-3(4H)-one (8.0 g, 79%), mp: 126-128.5° C.

The mixture of 6-(2-hydroxypropyl)-2H-1,4-benzoxazin-3(4H)-one (2.76 g, 12.5 mmol) and 4-fluoro-3-methyl-1-benzothiophene-2-carbaldehyde (1.94 g, 10.0 mmol) and ethyl acetate containing 15 v/v % HCl (25 mL) was stirred overnight. The precipitate was filtered and washed with diethyl ether (2×10 mL) to give 6-(4-fluoro-3-methyl-1-benzothiophen-2-yl)-3,8-dimethyl-1,6,8,9-tetrahydroisochromeno[7,6-b][1,4]oxazin-2(3H)-one (3, 4.0 g, ca. 100%).

(3) To the solution of 6-(4-fluoro-3-methyl-1-benzothiophen-2-yl)-3,8-dimethyl-1,6,8,9-tetrahydroisochromeno[7,6-b][1,4]oxazin-2(3H)-one (3, 3.97 g, ca. 10 mmol) in a mixture of acetone (140 mL) and toluene (60 mL) was added dropwise Jones reagent [19.5 mL, an aqueous solution of chromium trioxide (2.7 mmol/mL) and sulfuric acid (4.2 mmol/mL)].

The mixture was stirred for 2 hours at room temperature. Methanol (15 mL) was added and the solution was decanted from the inorganic precipitate, which was washed with acetone (2×20 mL). The combined organic layer was evaporated, water (75 mL) was added to the residue and the mixture was stirred for 30 minutes. The precipitate was filtered, washed with water (2×15 mL) and dried to give diketone 4 (3.8 g, 92%). Mp: 213-217° C.

(4) Perchloric acid (7.24 mL, 89 mmol, 70% aqueous solution) was added to a solution of diketone 4 (3.66 g, 8.9 mmol) in ethyl acetate (80 mL) under intense stirring and the mixture was stirred overnight. The crystalline product was filtered, washed with diethyl ether (2×5 mL), and dried to give 2-benzpyrylium salt 5 (3.21 g, 73%). Mp: 260-266° C.

(5) 2-Benzpyrylium salt (5, 3.2 g, 6.5 mmol) was added slowly to hydrazine hydrate (0.97 g, 19.4 mmol) in IPA (35 mL) at −10° C. The mixture was stirred for 30 minutes at ca. 0° C. and overnight at room temperature. Water was added (75 mL), the mixture was stirred for 1 hour, the crystalline product was filtered, washed with water (2×10 mL), recrystallized from a mixture of methanol and toluene (1:2) and dried to give 6-(4-fluoro-3-methyl-1-benzothiophen-2-yl)-3,9-dimethyl-1,6,9,10-tetrahydro[1,4]oxazino[3,2-h][2,3]benzodiazepin-2(3H)-one (6, 2.4 g, 92%). Mp: 259-262° C.

IR (KBr, cm$^{-1}$): 3053, 1706, 1506, 1370, 1300. $^1$H NMR (DMSO-d$_6$, 400 MHz): δ 11.06 (br s, 1H), 7.81 (m, 1H), 7.43 (m, 1H), 7.18 (m, 1H), 6.96/6.95 (s, 1H), 6.87/6.84 (s, 1H), 4.74/4.68 (q, J=6.9 Hz, 1H), 3.55 (d, J=12.4 Hz, 1H), 2.85 (d, J=12.2 Hz, 1H), 2.18/2.13 (d, J=2.3 Hz, 3H), 2.08 (s, 3H), 1.41/1.37 (d, J=6.8 Hz, 3H) ppm. $^{13}$C NMR (DMSO-d$_6$, 125 MHz): 167.44, 167.24, 158.70 (d, J=251.0 Hz), 154.74, 154.73, 152.25, 152.17, 142.52, 142.29, 141.56 (d, J=6.5 Hz), 136.75, 136.72, 133.62 (d, J=8.5 Hz), 131.75, 131.72, 130.50, 129.06 (d, J=14.7 Hz), 126.68, 126.61, 124.67, 124.49, 119.01, 116.48, 113.14, 113.04, 110.44 (d, J=20.4 Hz), 72.92, 72.77, 37.25, 25.61, 22.72, 16.27, 15.95, 15.79 (d, J=4.0 Hz) ppm. Elementary analysis calculated: C, 64.85; H, 4.45; N, 10.31; S, 7.87. Found: C, 63.59; H, 4.85; N, 9.72; S, 7.71.

Preparation of 1-(4-hydroxy-3-nitrophenyl)propan-2-one (1) used as the starting material in Step (1) was performed as follows:

(a) The solution of (4-hydroxyphenyl)acetic acid (4.65 g, 300 mmol) in glacial acetic acid (366 mL) was cooled to 10-15° C., and nitric acid (100.5 mL, 65 w/w %) was added dropwise over a period of 1 hour. A precipitate was formed, and the mixture was stirred for 90 min at 10-15° C. Cold water (1100 mL) was added and stirred for 1 hour at 10-15° C. The precipitate was filtered, washed with cold water (5×30 mL), and dried. 1-(4-Hydroxy-3-nitrophenyl)acetic acid was obtained (36.1 g, 62%), mp: 145-150° C.

(b) The mixture of 1-(4-hydroxy-3-nitrophenyl)acetic acid (78.2 g, 396.7 mmol) in acetic anhydride (400 mL, 4.24 mol) was stirred for 1 hour at room temperature, and pyridine (120.5 mL, 1.508 mol) was added dropwise over a period of 45 minutes. The mixture was then stirred for 1 hour at room temperature and refluxed for further 4 hours. The mixture was then evaporated, washed with toluene (3×10 mL), and evaporated. (Z)-2-(4-hydroxy-3-nitrophenyl)-1-methylethenyl acetate was obtained as an oil (109 g).

(c) The mixture of (Z)-2-(4-hydroxy-3-nitrophenyl)-1-methylethenyl acetate (54.3 g, 198 mmol), ethanol (240 mL) and concentrated hydrochloric acid (24.1 mL) was refluxed for 6 hours. The mixture was then stirred for 2 hours, filtered, washed with ethanol (2×5 mL). The solid obtained was recrystallized from a methanol-IPA 1:5 mixture. 1-(4-Hydroxy-3-nitrophenyl)propan-2-one was obtained (28.0 g, 72%), mp: 95-98.5° C.

Preparation of 4-fluoro-3-methyl-1-benzothiophene-2-carbaldehyde used in Step (2) was performed as follows:

(a) The mixture of a solution of 1-(2,6-difluorophenyl)ethanone (10.0 g, 0.064 mol) in DMF (100 mL), potassium carbonate anhydrous (11 g, 0.082 mol) and methylthio glycolate (6.0 mL, 0.064 mol) was stirred at room temperature overnight and then at 60-65° C. over a period of 8 hours, and additionally 4 hours at 80° C. and after additionally 3.5 hours at 100° C. After the reaction was complete, water (1 L) was added, and the precipitate was dissolved. The mixture was extracted with 1,2-dichloroethane (4×100 mL), dried over $Na_2SO_4$, filtered and evaporated in vacuo. Methyl 4-fluoro-3-methyl-1-benzothiophene-2-carboxylate was obtained as brownish crystals (9.5 g, 65%).

(b) To the solution of methyl 4-fluoro-3-methyl-1-benzothiophene-2-carboxylate (9.49 g, 0.042 mol) in a mixture of ethanol and THF (178+51 mL) was added $CaCl_2$ (5.96 g, 0.054 mol) under stirring. It was cooled with an ice bath, then $NaBH_4$ (5.56 g, 0.147 mol) was added under stirring. The mixture was then stirred at room temperature for 5 hours, and cooled with an ice bath. Concentrated hydrochloric acid (9.39 mL) was added dropwise, then water (635 mL) was added. The pH was adjusted to 4 with HCl, and the mixture was left overnight. A precipitate formed, it was filtered, washed with water (5×20 mL) and dried. The filtrate was extracted with dichloromethane (3×150 mL), washed with a saturated solution of sodium carbonate (150 mL), dried over $Na_2SO_4$, filtered and evaporated in vacuo. (4-Fluoro-3-methyl-1-benzothiophen-2-yl)methanol was obtained as yellowish crystals (7.71 g, 93%).

(c) To the solution of (4-fluoro-3-methyl-1-benzothiophen-2-yl)methanol (7.71 g, 0.039 mol) in DIPE (150 mL) was added DDQ (2,3-dichloro-5,6-dicyanobenzoquinone, 9.71 g, 0.043 mol) slowly. The black mixture was stirred overnight, and a precipitate formed. The crystals were filtered, washed with DIPE (5×10 mL), the filtrate was evaporated in vacuo, and then redissolved in ethyl acetate (50 mL). It was extracted with a saturated solution of $NaHCO_3$ (2×30 mL), washed with brine (2×30 mL), dried over $Na_2SO_4$, filtered and evaporated in vacuo. 4-Fluoro-3-methyl-1-benzothiophene-2-carbaldehyde was obtained as yellow crystals (7.86 g, ca. 100%), mp: 89-92° C.

EXAMPLE 2

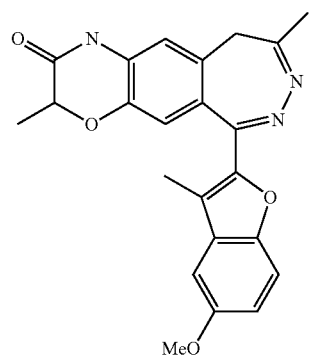

6-(5-Methoxy-3-methyl-1-benzofuran-2-yl)-3,9-dimethyl-1,10-dihydro[1,4]oxazino[3,2-h][2,3]benzodiazepin-2(3H)-one

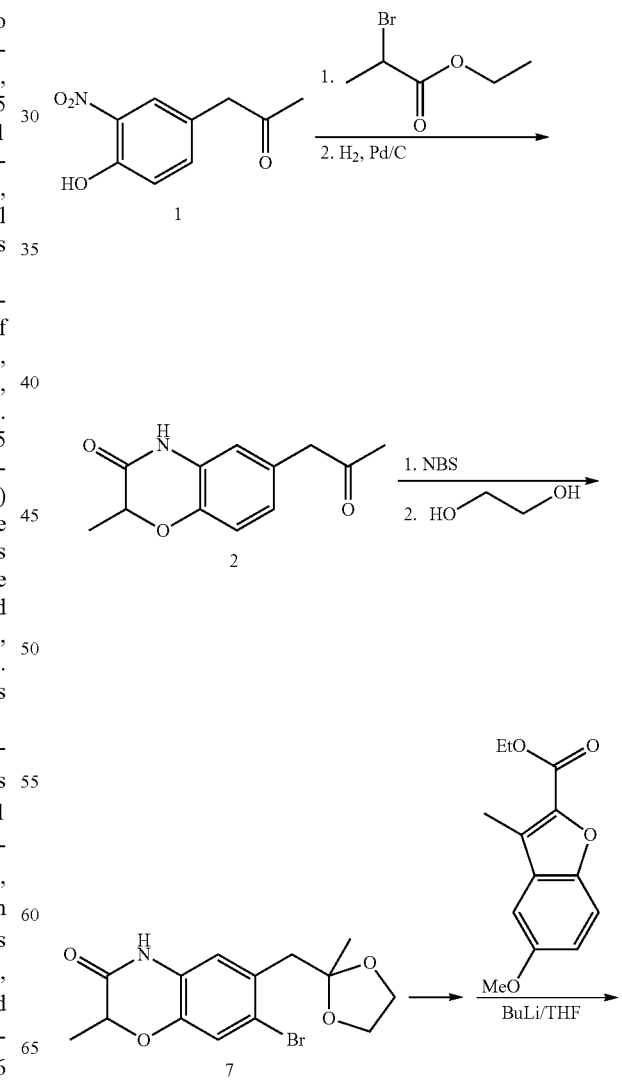

-continued

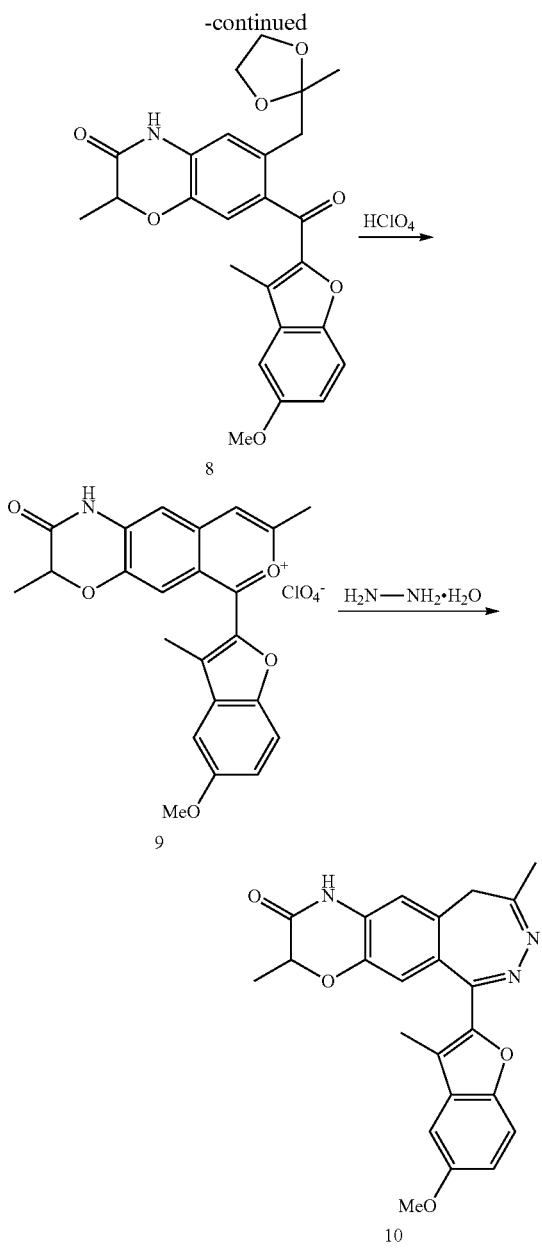

(1) N-bromosuccinimide (12.18 g, 69 mmol) was added slowly to a solution of 2-methyl-6-(2-oxopropyl)-2H-1,4-benzoxazin-3(4H)-one (2, 15.0 g, 69 mmol, see Example 1) in methanol (65 mL) at 0° C. over a period of 1.5 hours under intense cooling in ice bath. The solvent was evaporated in vacuo, the residue was triturated with water (200 mL), the solid product was filtered to give 7-bromo-2-methyl-6-(2-oxopropyl)-2H-1,4-benzoxazin-3(4H)-one (18.4 g, 90%) brownish crystals. Mp: 145-149° C.

(2) The mixture of 7-bromo-2-methyl-6-(2-oxopropyl)-2H-1,4-benzoxazin-3(4H)-one (13.2 g, 44 mmol), ethylene glycole (11.1 mL, 200 mmol), p-toluenesulfonic acid monohydrate (0.84 g, 4.4 mmol) and toluene (500 mL) was refluxed for 4 hours. The reaction mixture was cooled, poured on a mixture of ice-water (500 mL) and aqueous Na$_2$CO$_3$ solution (5 w/w %, 100 mL). The layers were separated, the aqueous layer was extracted with ethyl acetate (2×100 mL), the organic layers were combined and washed with water, dried and evaporated. The residue was recrystallized from DIPE to give 7-bromo-2-methyl-6-[(2-methyl-1,3-dioxolan-2-yl)methyl]-2H-1,4-benzoxazin-3(4H)-one (7, 12.9 g, 71%) yellowish crystals. Mp: 133-138° C.

(3) A solution of 7-bromo-2-methyl-6-[(2-methyl-1,3-dioxolan-2-yl)methyl]-2H-1,4-benzoxazin-3(4H)-one (7, 3.3 g, 9.6 mmol) in THF (250 mL) was cooled to −70° C., and hexyllithium in hexane (9.6 mL, 24 mmol) was added dropwise at −50° C., and stirred for 10 minutes. A solution of ethyl 5-methoxy-3-methyl-1-benzofuran-2-carboxylate (2.25 g, 9.6 mmol) in THF (30 mL) was cooled to −70° C. and added dropwise to the reaction mixture and it was stirred for 1.5 hours at −50-(−40)° C. It was then allowed to warm to −5° C. slowly, saturated ammonium chloride solution was added dropwise and the mixture was stirred for 30 minutes. The mixture was extracted with ethyl acetate (2×100 mL), the organic layer was dried and evaporated in vacuo to give 7-[(5-methoxy-3-methyl-1-benzofuran-2-yl)carbonyl]-2-methyl-6-[(2-methyl-1,3-dioxolan-2-yl)methyl]-2H-1,4-benzoxazin-3(4H)-one (8, 2.18 g, 60%) off-white crystals. Mp: 180° C.

(4) Perchloric acid (0.805 g, 5.6 mmol, 70% aqueous solution) was added dropwise to a solution of 7-[(5-methoxy-3-methyl-1-benzofuran-2-yl)carbonyl]-2-methyl-6-[(2-methyl-1,3-dioxolan-2-yl)methyl]-2H-1,4-benzoxazin-3(4H)-one (8, 2.14 g, 4.7 mmol) in ethanol (40 mL) under intense stirring, and the mixture was stirred for 1 hour. It was cooled to 15° C., the crystalline product was filtered, washed with ethanol, and dried to give 2-benzpyrylium salt 9 (2.72 g).

(5) 2-Benzpyrylium salt 9 (2.72 g, 5.55 mmol) was added slowly to a solution of hydrazine hydrate (0.834 g, 16.6 mmol) in IPA (60 mL) at −5° C. The mixture was stirred for 30 minutes at ca. 0° C. and overnight at room temperature. Water was added (240 mL) and the crystalline product was filtered, washed with water (3×10 mL) and recrystallized from a mixture of DMF and water to give 6-(5-methoxy-3-methyl-1-benzofuran-2-yl)-3,9-dimethyl-1,10-dihydro[1,4]-oxazino[3,2-h][2,3]benzodiazepin-2(3H)-one (10, 2.3 g, 49%). Mp: 252-255° C.

IR (KBr, cm$^{-1}$): 3080, 1712, 1511, 1372, 1303, 1212. $^1$H NMR (DMSO-d$_6$, 500 MHz): δ 11.01 (br s, 1H), 7.44 (dd, J$_1$=0.5-0.4 Hz, J$_2$=9.0-8.8 Hz), 7.20-7.19 (d, J=3.0-2.8 Hz, 1H), 6.96 (dd, J$_1$=2.6 Hz, J$_2$=8.9 Hz, 1H), 6.93-6.92 (s, 1H), 6.89-6.87 (s, 1H), 4.76-4.67 (q, J=6.8-6.7 Hz, 1H), 3.83 (s, 3H), 3.49-3.48 (d, J=12.5 Hz, 1H), 2.83-2.82 (d, J=12.2 Hz, 1H), 2.40-2.35 (s, 3H), 2.08-2.07 (s, 3H), 1.44-1.38 (d, J=6.7-6.8 Hz, 3H) ppm. $^{13}$C NMR (DMSO-d$_6$, 125 MHz): 167.42, 155.86, 154.59, 149.42, 148.94, 148.68, 142.24, 134.18, 131.39, 130.51, 123.21, 117.65, 116.87, 114.84, 112.97, 112.02, 102.54, 72.86, 55.84, 37.21, 22.66, 16.33, 9.69 ppm. Elementary analysis calculated: C, 68.47; H, 5.25; N, 10.42. Found: C, 67.41; H, 5.16; N, 10.35.

Preparation of ethyl 5-methoxy-3-methyl-1-benzofuran-2-carboxylate used in Step (3) was performed as follows:
(a) A suspension of NaH (4.4 g, 0.11 mol, 60% dispersion) in THF (50 mL) was added dropwise to a solution of 4-hydroquinone methyl ether (12.41 g, 0.1 mol) in THF (30 mL) at 20° C. under stirring. A solution of ethyl chloroacetate (18.11 g, 0.11 mol) in THF (25 mL) was added slowly to the mixture. The reaction mixture was then refluxed for 8 hours. After the reaction was complete, methanol (10 mL) was added, the solvent was evaporated, the residue was dissolved in ethyl acetate (400 mL), washed with water (40 mL), and brine (3×30 mL), dried over MgSO$_4$, filtered and evaporated. Ethyl 2-(4-methoxyphenoxy)-3-oxobutanoate was obtained as an oil (26.85 g).

(b) Polyphosporic acid (68 g, 0.7 mol) was added to ethyl 2-(4-methoxyphenoxy)-3-oxobutanoate (26.8 g, ca. 0.010 mol) and refluxed at 110-120° C. for 2 hours. The reaction mixture was poured on water (220 mL) and extracted with ethyl acetate (2×150 mL). The aqueous layer was further extracted with toluene (150 mL). The organic layers were combined and washed with brine (2×30 mL), stirred with charcoal, filtered, dried over MgSO$_4$, filtered and evaporated. The residue was recrystallized from methanol. Ethyl 5-methoxy-3-methyl-1-benzofuran-2-carboxylate was obtained as colorless crystals (25.0 g, 44%), mp: 98-104° C.

EXAMPLE 3

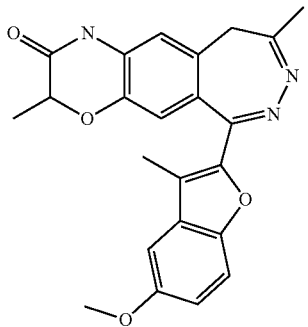 [SMILES: COc1ccc2oc(C3=NN=C(C)Cc4cc5c(cc43)OC(C)C(=O)N5)c(C)c2c1]

(−)-6-(5-Methoxy-3-methyl-1-benzofuran-2-yl)-3,9-dimethyl-1,10-dihydro[1,4]oxazino[3,2-h][2,3]benzodiazepin-2(3H)-one The title compound was obtained after chiral HPLC separation of 6-(5-methoxy-3-methyl-1-benzofuran-2-yl)-3,9-dimethyl-1,10-dihydro[1,4]oxazino[3,2-h][2,3]benzodiazepin-2(3H)-one described in Example 2.

Chiral chromatographic conditions were as follows: chromatographic column: Chiralpak AD (20 µm, d=5 cm, L=50 cm); eluent: EtOH-IPA (gradient: 100-0→0-100), 25 mL/min. The title compound was the first eluting peak. Chiral purity (HPLC): >99.9%.

Mp: 250-258° C. [α]$_D$=−17.31° (c=0.5; IPA, MeOH, DMSO). IR, $^1$H NMR and $^{13}$C NMR data are identical with those described for the racemic compound in Example 2. Elementary analysis calculated: C, 68.47; H, 5.25; N, 10.42. Found: C, 68.00; H, 5.32; N, 10.31.

EXAMPLE 4

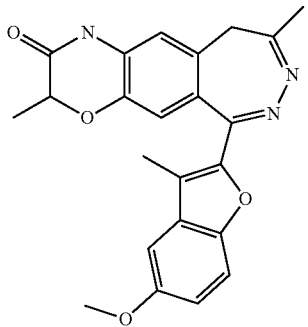 [SMILES: COc1ccc2oc(C3=NN=C(C)Cc4cc5c(cc43)OC(C)C(=O)N5)c(C)c2c1]

(+)-6-(5-Methoxy-3-methyl-1-benzofuran-2-yl)-3,9-dimethyl-1,10-dihydro[1,4]oxazino[3,2-h][2,3]benzodiazepin-2(3H)-one The title compound was obtained after chiral HPLC separation of 6-(5-methoxy-3-methyl-1-benzofuran-2-yl)-3,9-dimethyl-1,10-dihydro[1,4]oxazino[3,2-h][2,3]benzodiazepin-2(3H)-one described in Example 2.

Chiral chromatographic conditions were as follows: chromatographic column: Chiralpak AD (20 µm, d=5 cm, L=50 cm); eluent: EtOH-IPA (gradient: 100-0→0-100), 25 mL/min. The title compound was the second eluting peak. Chiral purity (HPLC): >99.9%.

Mp: 254-258° C. [α]$_D$=+15.53° (c=0.5; IPA, MeOH, DMSO). IR, $^1$H NMR and $^{13}$C NMR data are identical with those described for the racemic compound in Example 2. Elementary analysis calculated: C, 68.47; H, 5.25; N, 10.42. Found: C, 67.96; H, 5.46; N, 10.19.

EXAMPLE 5

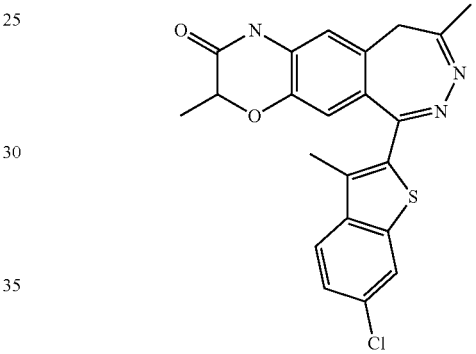

6-(6-Chloro-3-methyl-1-benzothiophen-2-yl)-3,9-dimethyl-1,10-dihydro[1,4]oxazino[3,2-h][2,3]benzodiazepin-2(3H)-one (1) The mixture of 6-chloro-3-methyl-1-benzothiophene-2-carbaldehyde (2.21 g, 10.0 mmol) in ethyl acetate (18 mL) and 6-(2-hydroxypropyl)-2H-1,4-benzoxazin-3(4H)-one (2.11 g, 10.0 mmol) was ice cooled and a solution of ethyl acetate containing 15 V/V % HCl (10.7 mL) was added. The mixture was stirred over a period of 5 hours with ice cooling, and for further 22 hours at room temperature. After the reaction was complete, diethyl ether (20 mL) was added with ice cooling, and the mixture stirred for 15 minutes. The mixture was then filtered and washed with a mixture of diethyl ether and ethyl acetate (1:1, 15 mL), washed with diethyl ether (2×15 mL), and dried to give a crystalline product (3.1 g, 75%). Mp: 299-302° C.

(2) To the solution of 6-(6-chloro-3-methyl-1-benzothiophen-2-yl)-3,8-dimethyl-1,6,8,9-tetrahydroisochromeno[7,6-b][1,4]oxazin-2(3H)-one (2.88 g, 7 mmol) thus obtained in acetone-toluene (400 mL+150 mL) was added dropwise Jones reagent [10 mL, an aqueous solution of chromium trioxide (2.7 mmol/mL) and sulfuric acid (4.2 mmol/mL)] and the mixture was stirred for 2 hours at 35-37° C. Then IPA (10 mL) was added, the solvents were evaporated in vacuo, and the residue was triturated with ice water (300 mL). The precipitate was filtered, washed with water and dried, then purified by column chromatography to give crystalline diketone (1.7 g, 57%). Mp: 235-237° C.

(3) Perchloric acid (0.55 mL, 6 mmol, 70% aqueous solution) was added to a solution of the diketone thus obtained (1.63 g, 4 mmol) in ethyl acetate (80 mL) under intense stirring at 130° C. When the addition was complete, the mixture was refluxed for 15 minutes. Ethyl acetate was added (40 mL) and the mixture was stirred for 15 minutes at 110° C. The mixture was then cooled, filtered, washed with ethyl acetate twice and with diethyl ether twice, and dried to give 2-benzpyrylium salt (2.0 g). Mp: 291-293° C.

(4) Hydrazine hydrate (0.74 mL, 15 mmol) was added slowly at room temperature to the solution of the 2-benzpyrylium salt obtained above (1.95 g, ca. 4 mmol) in IPA (40 mL), and the mixture was stirred for 8 hours. After the reaction was complete, pH was adjusted to 6 with HCl (1M), and the solvents were evaporated in vacuo. Water (50 mL) was added to the residue, it was filtered, and washed with water twice then with cold acetonitrile and diethyl ether, finally dried over $P_2O_5$ in vacuo to give the title compound (1.42 g, 88%). Mp: 291-293° C.

IR (KBr, $cm^{-1}$): 3073, 2939, 1711, 1619, 1588, 1506, 1374, 1303, 1105. $^1$H NMR (DMSO-$d_6$, 500 MHz): δ 11.06 (s, 2H), 8.15 (s, 2H), 7.82 (d, 1H, J=8.4 Hz), 7.81 (d, 1H, J=8.6 Hz), 7.46 (d, 2H, J=8.6 Hz), 6.97 (s, 1H), 6.96 (s, 1H), 6.86 (s, 1H), 6.84 (s, 1H), 4.73 (q, 1H, J=6.8 Hz), 4.68 (q, 1H, J=6.8 Hz), 3.53 (d, 2H, J=12.5 Hz), 2.87 (d, 1H, J=12.5 Hz), 2.86 (d, 1H, J=12.5 Hz), 2.08 (s, 6H), 2.06 (s, 3H), 2.01 (s, 3H), 1.41 (d, 3H, J=6.8 Hz), 1.36 (d, 3H, J=6.8 Hz) ppm. $^{13}$C NMR (DMSO-$d_6$, 125 MHz): 167.44, 167.20, 154.78, 154.75, 152.50, 152.40, 142.45, 142.16, 140.26, 139.68, 139.62, 137.08, 137.06, 133.80, 133.69, 132.17, 131.66, 130.58, 130.56, 125.01, 124.98, 124.45, 124.26, 124.16, 122.01, 122.00, 116.64, 113.12, 113.01, 72.93, 72.78, 37.23, 22.73, 16.30, 15.90, 13.80, 13.74 ppm. Elementary analysis calculated: C, 62.33; H, 4.28; Cl, 8.36; N, 9.91; S, 7.56. Found: C, 62.03; H, 4.30; Cl, 8.16; N, 9.83; S, 7.63.

EXAMPLE 6

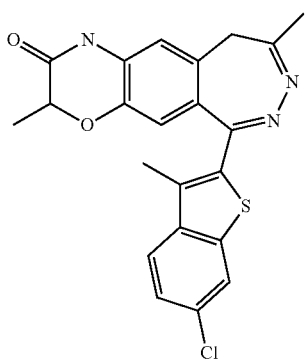 [SMILES: CC1=NN=C(c2sc3cc(Cl)ccc3c2C)c2cc3c(cc2C1)NC(=O)C(C)O3]

(+)-6-(6-Chloro-3-methyl-1-benzothiophen-2-yl)-3,9-dimethyl-1,10-dihydro[1,4]oxazino[3,2-h][2,3]benzodiazepin-2(3H)-one The title compound was obtained after chiral HPLC separation of 6-(6-chloro-3-methyl-1-benzothiophen-2-yl)-3,9-dimethyl-1,10-dihydro[1,4]oxazino[3,2-h][2,3]benzodiazepin-2(3H)-one described in Example 5.

The chiral chromatographic conditions were analogous with the method described in Examples 3 and 4.

Mp: 295-296° C. $[α]_D$=+19.0° (c=1, DMSO). IR, $^1$H NMR and $^{13}$C NMR data are identical with those described for the racemic compound in Example 5. Elementary analysis calculated: C, 62.33; H, 4.28; Cl, 8.36; N, 9.91; S, 7.56. Found: C, 62.08; H, 4.35; Cl, 8.40; N, 9.86; S, 7.60.

EXAMPLE 7

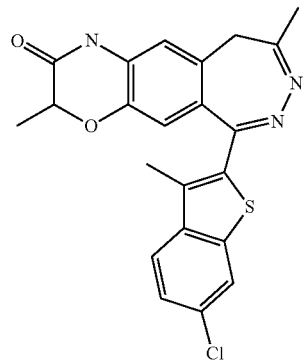 [SMILES: CC1=NN=C(c2sc3cc(Cl)ccc3c2C)c2cc3c(cc2C1)NC(=O)C(C)O3]

(−)-6-(6-Chloro-3-methyl-1-benzothiophen-2-yl)-3,9-dimethyl-1,10-dihydro[1,4]oxazino[3,2-h][2,3]benzodiazepin-2(3H)-one The title compound was obtained after chiral HPLC separation of 6-(6-chloro-3-methyl-1-benzothiophen-2-yl)-3,9-dimethyl-1,10-dihydro[1,4]oxazino[3,2-h][2,3]benzodiazepin-2(3H)-one described in Example 5.

The chiral chromatographic conditions were analogous with the method described in Examples 3 and 4.

Mp: 294-295° C. $[α]_D$=−19.7° (c=1, DMSO). IR, $^1$H NMR and $^{13}$C NMR data are identical with those described for the racemic compound in Example 5. Elementary analysis calculated: C, 62.33; H, 4.28; Cl, 8.36; N, 9.91; S, 7.56. Found: C, 62.00; H, 4.30; Cl, 8.40; N, 9.84; S, 7.30.

EXAMPLE 8

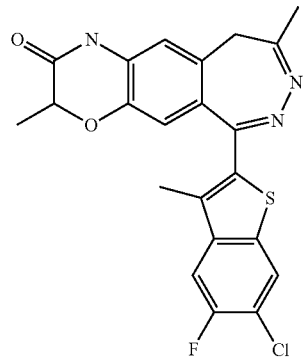 [SMILES: CC1=NN=C(c2sc3cc(Cl)c(F)cc3c2C)c2cc3c(cc2C1)NC(=O)C(C)O3]

6-(6-Chloro-5-fluoro-3-methyl-1-benzothiophen-2-yl)-3,9-dimethyl-1,10-dihydro[1,4]oxazino[3,2-h][2,3]benzodiazepin-2(3H)-one (1) The mixture of 6-chloro-5-fluoro-3-methyl-1-benzothiophene-2-carbaldehyde (2.49 g, 10.8 mmol) in ethyl acetate (22 mL) and 6-(2-hydroxypropyl)-2H-1,4-benzoxazin-3(4H)-one (2.39 g, 10.8 mmol) and a solution of ethyl acetate containing 15 V/V % HCl (11 mL) was stirred overnight at room temperature. After the reaction was complete, the mixture was filtered and washed with ethyl acetate (3×5 mL), and dried to give purple crystals (2.84 g, 75%).

(2) To the suspension of 6-(6-chloro-5-fluoro-3-methyl-1-benzothiophen-2-yl)-3,8-dimethyl-1,6,8,9-tetrahydroisochromeno[7,6-b][1,4]oxazin-2(3H)-one (2.84 g, 6.6 mmol) thus obtained in acetone (57 mL) was added dropwise Jones reagent [8.2 mL, an aqueous solution of chromium trioxide (2.7 mmol/mL) and sulfuric acid (4.2 mmol/mL)] with ice cooling, and the mixture was stirred overnight at room temperature. The precipitate was filtered, washed with acetone and water, and dried. The filtrate was evaporated, washed with water and dried. The combined crystals were dissolved in a mixture of acetone (51 mL) and toluene (5.7 mL), and Jones. reagent (8.2 mL) was added dropwise again at room temperature. The mixture was stirred for 2 hours at room temperature, and water was added (200 mL), and after 10 hours the precipitate was filtered, washed with water, and dried to give off-white crystals (2.0 g, 68%). Mp: 243-245° C.

(3) Perchloric acid (0.4 mL, 4.6 mmol, 70% aqueous solution) was added to the solution of diketone (2.04 g, 4.6 mmol) obtained above in ethyl acetate (41 mL) under intense stirring at 130° C. After the addition was complete, the mixture was refluxed for 15 minutes. The mixture was then cooled, filtered, washed with ethyl acetate (3×5 mL), and dried to give 2-benzpyrylium salt (2.16 g, 89%). Mp: 281-283° C.

(4) Hydrazine hydrate (0.55 mL, 11 mmol) was added slowly at room temperature to the solution of the 2-benzpyrylium salt (2.16 g, 4.1 mmol) obtained above in IPA (43 mL), and the mixture was stirred overnight. After the reaction was complete, the precipitate was filtered, washed with IPA (3×5 mL), and dried. It was the recrystallized from DMF to give the title compound (1.24 g, 69%) as white crystals. Mp: 296-298° C.

IR (KBr, cm$^{-1}$): 3042, 1710, 1506, 1375, 1306. $^1$H NMR (DMSO-d$_6$, 500 MHz): δ 11.06 (br s, 1H), 8.32 (d, J=6.8 Hz, 1H), 7.87/7.84 (d, J=10.3 Hz, 1H), 6.96-6.95 (s, 1H), 6.85-6.83 (s, 1H), 4.73-4.68 (q, J=6.8 Hz, 1H), 3.53 (d, J=12.5 Hz, 1H), 2.85 (d, J=12.3 Hz, 1H), 2.08 (s, 3H), 2.03-1.98 (s, 3H), 1.41-1.36 (d, J=6.8 Hz, 3H) ppm. Elementary analysis calculated: C, 59.80; H, 3.88; Cl, 8.02; N, 9.51; S, 7.20. Found: C, 59.17; H, 4.00; Cl, 7.96; N, 9.58; S, 7.20.

EXAMPLE 9

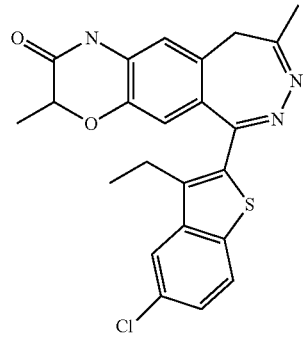 [SMILES: CCc1c(C2=NN=C(C)Cc3cc4c(cc32)OC(C)C(=O)N4)sc2ccc(Cl)cc12]

6-(5-Chloro-3-ethyl-1-benzothiophen-2-yl)-3,9-dimethyl-1,10-dihydro[1,4]oxazino[3,2-h][2,3]benzodiazepin-2(3H)-one (1) To the solution of freshly prepared ZnCl$_2$ in dioxane (15 mL) was added 5-chloro-3-ethyl-1-benzothiophene-2-carbaldehyde (1.86 g, 8.3 mmol) and 6-(2-hydroxypropyl)-2H-1,4-benzoxazin-3(4H)-one (1.77 g, 8 mmol), and the mixture was ice cooled. A solution of dioxane containing 15 V/V % HCl (11 mL) was added and kept in ice for 20 minutes, and then stirred for 3.5 hours at room temperature. After the reaction was complete, the mixture was poured into ice water (150 mL), stirred, filtered and washed with water, and dried to give a crystalline product (3.62 g) crystals.

(2) The suspension of silica gel (33 g), Jones reagent [12 mL, an aqueous solution of chromium trioxide (2.7 mmol/mL) and sulfuric acid (4.2 mmol/mL)] in dichloromethane (110 mL) and acetone (28 mL) was ice cooled, and 6-(5-chloro-3-ethyl-1-benzothiophen-2-yl)-3,8-dimethyl-1,6,8,9-tetrahydroisochromeno[7,6-b][1,4]oxazin-2(3H)-one (3.46 g, 8 mmol) obtained above was added in one portion, and the mixture was stirred for 15 minutes. IPA (30 mL) was added and after 5 minutes methanol (10 mL) was added, and the mixture was stirred for 10 minutes. The solid was filtered, eluted on silica gel with a solution of dichloromethane/methanol (10:1), and the filtrate was partly evaporated to a volume of 100 mL. Water (250 mL) was added and the organic solvent was evaporated. Water (150 mL) was added and stirred for 10 minutes, filtered, washed with water 3 times, and dried. Purification by flash chromatography gave a crystalline product (2.2 g, 62%). Mp: 190-192° C.

(3) Perchloric acid (0.76 mL, ~8.8 mmol, 70% aqueous solution) was added to a hot solution of the diketone (2.1 g, 4.8 mmol) obtained above in ethyl acetate (80 mL). After the addition was complete, the mixture was refluxed for 25 minutes, then cooled, filtered, washed with ethyl acetate and diethyl ether, and dried. to give 2-benzpyrylium salt (2.32 g, 93%). Mp: 250-252° C.

(4) Hydrazine hydrate (0.63 mL, 13 mmol) was added slowly at room temperature to the solution of the 2-benzpyrylium salt (2.24 g, 4.3 mmol) obtained above in IPA (30 mL), and the mixture was stirred overnight. After the reaction was complete, pH was adjusted to 5 with HCl (4.5 mL, 1 M), and evaporated. Water was added to the residue, it was stirred, filtered, washed with water 3 times, then with acetonitrile (3×3 mL), diethyl ether (2×8 mL), and dried over $P_2O_5$ to give the title compound (1.59 g, 85%). Mp: 233-234° C.

IR (KBr, $cm^{-1}$): 2938, 2871, 1711, 1621, 1594, 1508, 1370, 1299, 1102. $^1$H NMR (DMSO-$d_6$, 400 MHz): δ 11.06 (s, 2H), 8.02 (d, 2H, J=8.6 Hz), 7.93 (d, 1H, J=2.0 Hz), 7.92 (d, 1H, J=2.0 Hz), 7.46 (dd, 2H, J=8.6, 2.0 Hz), 6.96 (s, 1H), 6.95 (s, 1H), 6.85 (s, 1H), 6.84 (s, 1H), 4.71 (q, 1H, J=6.8 Hz), 4.68 (q, 1H, J=6.8 Hz), 3.55 (d, 2H, J=12.4 Hz), 2.85 (d, 1H, J=12.3 Hz), 2.84 (d, 1H, J=12.3 Hz), 2.68 (m, 2H), 2.64 (m, 2H), 2.08 (s, 6H), 1.40 (d, 3H, J=6.8 Hz), 1.36 (d, 3H, J=6.8 Hz), 1.03 (t, 3H), 1.00 (t, 3H) ppm. Elementary analysis calculated: C, 63.08; H, 4.60; Cl, 8.10; N, 9.59; S, 7.32. Found: C, 62.58; H, 4.63; Cl, 8.17; N, 9.64; S, 7.29.

EXAMPLE 10

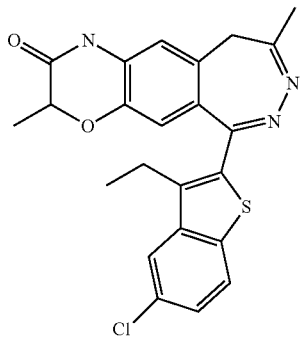 [SMILES: CCc1c(C2=NN=C(C)Cc3cc4c(cc32)OC(C)C(=O)N4)sc2ccc(Cl)cc12]

(+)-6-(5-Chloro-3-ethyl-1-benzothiophen-2-yl)-3,9-dimethyl-1,10-dihydro[1,4]oxazino[3,2-h][2,3]benzodiazepin-2(3H)-one The chiral chromatographic conditions were analogous with the method described in Examples 3 and 4.

Mp: 233-235° C. $[α]_D$=+17.9° (c=1, DMSO). IR, $^1$H NMR and $^{13}$C NMR data are identical with those described for the racemic compound in Example 9. Elementary analysis calculated: C, 63.08; H, 4.60; Cl, 8.10; N, 9.59; S, 7.32. Found: C, 62.89; H, 4.62; Cl, 8.04; N, 9.62; S, 7.28.

EXAMPLE 11

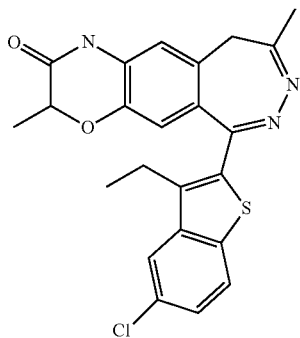 [SMILES: CCc1c(C2=NN=C(C)Cc3cc4c(cc32)OC(C)C(=O)N4)sc2ccc(Cl)cc12]

(−)-6-(5-Chloro-3-ethyl-1-benzothiophen-2-yl)-3,9-dimethyl-1,10-dihydro[1,4]oxazino[3,2-h][2,3]benzodiazepin-2(3H)-one The chiral chromatographic conditions were analogous with the method described in Examples 3 and 4.

Mp: 234-236° C. $[α]_D$=−17.8° (c=1, DMSO). IR, $^1$H NMR and $^{13}$C NMR data are identical with those described for the racemic compound in Example 9. Elementary analysis calculated: C, 63.08; H, 4.60; Cl, 8.10; N, 9.59; S, 7.32. Found: C, 62.92; H, 4.60; Cl, 8.14; N, 9.63; S, 7.36.

EXAMPLE 12

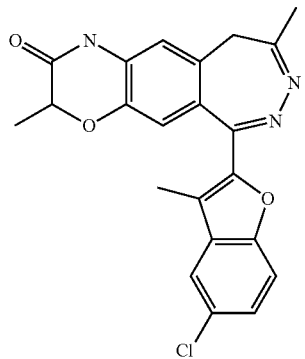 [SMILES: CC1=NN=C(c2oc3ccc(Cl)cc3c2C)c2cc3c(cc2C1)NC(=O)C(C)O3]

6-(5-Chloro-3-methyl-1-benzofuran-2-yl)-3,9-dimethyl-1,10-dihydro[1,4]oxazino[3,2-h][2,3]benzodiazepin-2(3H)-one (1) To a solution of 7-bromo-2-methyl-6-[(2-methyl-1,3-dioxolan-2-yl)methyl]-2H-1,4-benzoxazin-3(4H)-one (140 mg, 0.41 mmol) in toluene (10 mL) butyllithium in hexane (0.4 mL, 10 mmol, 2.5 M) was added dropwise at (−50)–(−45°) C., and the mixture was allowed to warm slowly to −30° C. and stirred for 45 minutes. The mixture was then cooled to −70° C. and 5-chloro-N-methoxy-N,3-dimethyl-1-benzofuran-2-carboxamide (140 mg, 0.55 mmol) was added slowly, and stirred for 2 hours at (−30)-(−40)° C. After the reaction was complete, the mixture was allowed to warm to −5° C., a saturated solution of ammonium chloride (5 mL) was added and stirred for 10 minutes. The mixture was then extracted with ethyl acetate (10 mL), washed with brine, dried over $MgSO_4$, filtered and evaporated in vacuo. The residue was recrystallized from ethyl acetate to give white crystals (40 mg, 22%). Mp: 210-217° C.

(2) Perchloric acid (0.025 mL, 0.31 mmol, 70% aqueous solution) was added to a solution of 7-[(5-chloro-3-methyl-1-benzofuran-2-yl)carbonyl]-2-methyl-6-[(2-methyl-1,3-dioxolan-2-yl)methyl]-2H-1,4-benzoxazin-3(4H)-one (70 mg, 0.15 mmol) obtained above in ethyl acetate (2 mL) and stirred at room temperature. After the reaction was complete, the crystals were filtered, and washed with diethyl ether to give 2-benzpyrylium salt (30 mg, 40%).

(3) The 2-benzpyrylium salt (120 mg, 0.24 mmol) thus obtained was added slowly at −10° C. to a solution of hydrazine hydrate (0.036 mL, 0.73 mmol) in IPA (2.5 mL). The mixture was stirred for 30 minutes at −10° C. and for additional 1 hour at 0° C. and 2 hours at room temperature. After the reaction was complete, water was added (15 mL)

and the mixture was stirred for 30 minutes, filtered, and washed with water (2×2 mL) to give the title compound (35 mg, 45%). Mp: 247-251° C.

IR (KBr, cm$^{-1}$): 3443, 1709, 1502, 1375, 1308. $^1$H NMR (DMSO-d$_6$, 500 MHz): δ 11.02 (br s, 1H), 7.81 (d, J=2.2 Hz, 1H), 7.59 (d, J=8.8 Hz, 1H), 7.39 (dd, J=1.7, 8.5 Hz, 1H), 6.94-6.93 (s, 1H), 6.93-6.90 (s, 1H), 4.77-4.68 (q, J=6.9 Hz, 1H), 3.50 (d, 12.3 Hz, 1H), 2.82 (d, J=12.3 Hz, 1H), 2.39-2.35 (s, 3H), 2.08 (s, 3H), 1.43-1.38 (d, J=6.8 Hz, 3H) ppm. $^{13}$C NMR (DMSO-d$_6$, 125 MHz): 167.44, 167.20, 154.72, 154.68, 152.21, 149.71, 149.58, 149.17, 149.13, 142.33, 141.84, 134.25, 134.09, 131.55, 131.53, 127.56, 125.74, 123.02, 122.88, 120.15, 120.12, 117.22, 117.19, 116.82, 116.77, 113.08, 113.05, 112.97, 93.17, 72.87, 72.77, 37.24, 22.67, 22.65, 16.35, 16.01, 9.54, 9.51 ppm. Elementary analysis calculated: C, 64.79; H, 4.45; Cl, 8.69; N, 10.30. Found: C, 63.48; H, 4.56; N, 9.99.

EXAMPLE 13

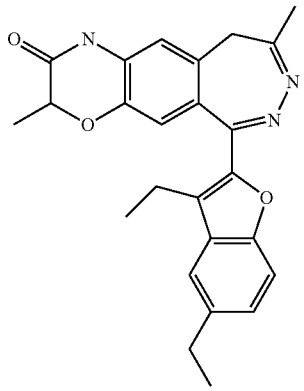 [SMILES: CCc1ccc2oc(C3=NN=C(C)Cc4cc5c(cc43)OC(C)C(=O)N5)c(CC)c2c1]

6-(3,5-Diethyl-1-benzofuran-2-yl)-3,9-dimethyl-1,10-dihydro[1,4]oxazino[3,2-h][2,3]benzodiazepin-2(3H)-one (1) To a solution of 7-bromo-2-methyl-6-[(2-methyl-1,3-dioxolan-2-yl)methyl]-2H-1,4-benzoxazin-3(4H)-one (2.4 g, 7 mmol) in THF (135 mL) utyllithium (7.5 mL, 19 mmol) was added dropwise at −78° C., and stirred for 20 minutes. A solution of methyl 3,5-diethyl-1-benzofuran-2-carboxylate (1.86 g, 8 mmol) in THF (5 mL) was added dropwise to the reaction mixture at −78° C., and stirred for 2 hours. The mixture was stirred for 1 hour at −50° C., then allowed to warm to −30° C. slowly, and a saturated solution of ammonium chloride (60 mL) was added. The mixture was then extracted with ethyl acetate (80 mL), washed with brine, dried over MgSO$_4$, filtered and evaporated in vacuo, and the residue was purified by column chromatography to give an oily product (1.9 g, 59%).

(2) Perchloric acid (0.56 mL, 70% aqueous solution) was added dropwise to a solution of 7-[(3,5-diethyl-1-benzofuran-2-yl)carbonyl]-2-methyl-6-[(2-methyl-1,3-dioxolan-2-yl)methyl]-2H-1,4-benzoxazin-3(4H)-one (1.77 g, 3.8 mmol) obtained above in ethyl acetate (15 mL) under intense stirring. After the addition was complete, the mixture was refluxed for 25 minutes. The mixture was then cooled, filtered, washed with ethyl acetate, with diethyl ether twice and dried. to give 2-benzpyrylium salt (1.6 g, 84%). Mp: 202-204° C.

(3) The solution of the pyrylium salt (1.52 g, 3 mmol) thus obtained in IPA (40 mL) was added slowly to hydrazine hydrate (0.5 mL). The mixture was stirred for 24 hours. After the reaction was complete, HCl (3 mL, 1 M) was added, the solvents were evaporated, the residue was washed with water, filtered, dissolved in ethyl acetate/dichloromethane (1:1), dried and evaporated. The residue was purified by column chromatography to give the title compound (0.75 g, 60%). Mp: 204-205° C.

IR (KBr, cm$^{-1}$): 2961, 1701, 1619, 1507, 1399, 1327, 1112, 1092, 1047. $^1$H NMR (DMSO-d$_6$, 400 MHz): δ 11.02 (s, 1H); 7.55 (m, 1H); 7.43 (d, 1H, J=8.5 Hz); 7.21 (dd, 1H, J=8.5, 1.2 Hz); 6.94, 6.93 (s, 1H); 6.84, 6.82 (s, 1H); 4.75, 4.67 (q, 1H, J=6.8 Hz); 3.51, 3.50 (d, 1H, J=12.4 Hz); 2.95, 2.92 (q, 2H); 2.84, 2.83 (d, 1H, J=12.3 Hz); 2.74 (q, 2H); 2.08 (s, 3H); 1.43, 1.37 (d, 3H, J=6.8 Hz); 1.27, 1.24 (t, 3H, J=7.4 Hz); 1.25 (t, 3H, J=7.4 Hz); ppm. $^{13}$C NMR (DMSO-d$_6$, 100 MHz): 167.39, 167.18; 154.59, 154.57; 152.55, 152.53; 149.44, 149.39; 148.03, 147.91; 142.19, 141.73; 138.69, 138.68; 134.06, 133.95; 131.45, 131.42; 128.93; 125.93, 125.91; 123.48, 123.45; 123.46, 123.35; 119.03, 119.01; 116.75, 116.67; 113.00, 112.94; 111.18; 72.86, 72.76; 37.25; 28.31; 22.64, 22.62; 17.29, 17.26; 16.42; 16.31, 16.03; 14.54, 14.49; ppm. (Two sets of signals with almost equal intensity appear in the spectra, which are due to the presence of conformational diastereomers.) Elementary analysis calculated: C, 72.27; H, 6.06; N, 10.11. Found: C, 71.85; H, 6.08; N, 9.90.

EXAMPLE 14

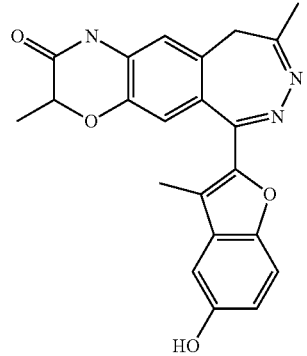 [SMILES: CC1=NN=C(c2oc3ccc(O)cc3c2C)c2cc3c(cc2C1)NC(=O)C(C)O3]

6-(5-Hydroxy-3-methyl-1-benzofuran-2-yl)-3,9-dimethyl-1,10-dihydro[1,4]oxazino[3,2-h][2,3]benzodiazepin-2(3H)-one A solution of boron tribromide in dichloromethane (40 mL, 1.0 M, 4.0 mmol) was added dropwise to a solution of 6-(5-methoxy-3-methyl-1-benzofuran-2-yl)-3,9-dimethyl-1,10-dihydro[1,4]oxazino[3,2-h][2,3]benzodiazepin-2(3H)-one (404 mg, 1 mmol, described in Example 2) in dichloromethane (50 mL) at 0° C. under stirring under argon atmosphere. After the addition was complete, the mixture was stirred for 4 hours at room temperature. The reaction mixture was poured on ice, pH was adjusted to 5-6 with a solution of sodium acetate, and the layers were separated. The aqueous layer was extracted with ethyl acetate (3×50 mL), dried over MgSO$_4$, filtered and evaporated in vacuo, then crystallized from a 1:1 mixture of water and acetone.

The solid obtained was washed with MTBE to give the title compound (0.23 g, 59%). Mp: 293-300° C.

IR (KBr, cm$^{-1}$): 3378, 3200, 1690, 1665, 1189. $^1$H NMR (DMSO-d$_6$, 500 MHz): δ 11.00 (br s, 1H), 9.26 (br s, 1H), 7.32 (d, J=8.6 Hz, 1H), 6.95 (d, 1H), 6.94-6.93 (s, 1H), 6.87-6.85 (s, 1H), 6.82 (dd, J=2.0, 8.6 Hz, 1H), 4.77-4.68 (q, J=7.0 Hz, 1H), 3.48 (d, J=12.5 Hz, 1H), 2.81 (d, J=12.3 Hz, 1H), 2.33-2.30 (s, 3H), 2.07 (s, 3H), 1.43-1.38 (d, J=6.8 Hz, 3H) ppm. $^{13}$C NMR (DMSO-d$_6$, 125 MHz): 167.42, 167.20, 154.56, 154.53, 153.53, 149.48, 149.45, 148.67, 148.53, 147.99, 147.97, 142.22, 141.76, 134.16, 134.00, 131.35, 130.65, 123.25, 123.11, 117.24, 117.20, 116.83, 114.92, 112.95, 112.86, 111.71, 104.38, 72.87, 72.77, 37.19, 22.65, 16.33, 16.02, 9.68 ppm. Elementary analysis calculated: C, 67.86; H, 4.92; N, 10.79. Found: C, 66.41; H, 4.95; N, 10.25.

The Examples described below were prepared from corresponding starting materials in a manner similar to the methods disclosed in the above Examples.

EXAMPLE 15

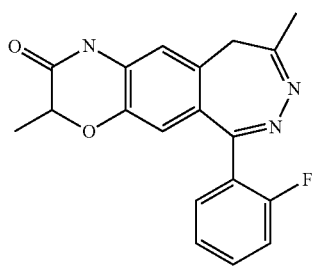 [SMILES: CC1=NN=C(c2ccccc2F)c2cc3c(cc2C1)NC(=O)C(C)O3]

6-(2-Fluorophenyl)-3,9-dimethyl-1,10-dihydro[1,4]oxazino[3,2-h][2,3]benzodiazepin-2(3H)-one The preparation of the title compound is analogous with the method described in Example 1. Mp: 260-262° C. IR (KBr, cm$^{-1}$): 3455, 1702, 1509, 1376, 1297, 761. $^1$H NMR (CDCl$_3$, 500 MHz): δ 9.18-9.11 (br s, 1H), 7.82 (m, 1H), 7.44 (m, 1H), 7.27 (m, 1H), 7.04 (m, 1H), 6.82-6.81 (s, 1H), 6.76-6.75 (s, 1H), 4.70-4.59 (m, 1H), 3.32 (d, J=12.5 Hz, 1H), 3.10 (d, J=12.3 Hz, 1H), 2.19 (s, 3H), 1.60-1.53 (d, J=6.8 Hz) ppm. Elementary analysis calculated: C, 67.65; H, 4.78; F, 5.63; N, 12.46. Found: C, 66.56; H, 4.90; N, 12.25.

EXAMPLE 16

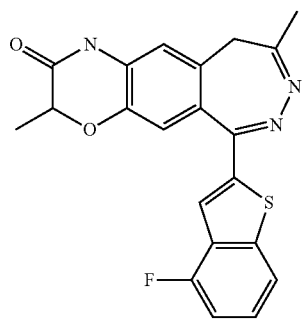 [SMILES: CC1=NN=C(c2cc3c(F)cccc3s2)c2cc3c(cc2C1)NC(=O)C(C)O3]

6-(4-Fluoro-1-benzo[b]thiophen-2-yl)-3,9-dimethyl-1,10-dihydro[1,4]oxazino[3,2-h][2,3]benzodiazepin-2(3H)-one The preparation of the title compound is analogous with the method described in Example 1. Mp: 303-306° C. IR (KBr, cm$^{-1}$): 3055, 1706, 1508, 1371, 1301, 769. $^1$H NMR (DMSO-d$_6$, 500 MHz): δ 11.06 (br s, 1H), 7.83 (d, J=8.2 Hz, 1H), 7.43 (m, 1H), 7.43-7.40 (d, J=0.7 Hz, 1H), 7.34-7.33 (s, 1H), 7.20 (m, 1H), 6.95-6.94 (s, 1H), 4.83-4.72 (q, J=7.0 Hz, 1H), 3.46-3.45 (d, J=12.6 Hz, 1H), 2.84-2.83 (d, J=12.5 Hz, 1H), 2.06 (s, 3H), 1.48-1.43 (d, J=6.6 Hz, 3H) ppm. Elementary analysis calculated: C, 64.11; H, 4.10; F, 4.83; N, 10.68; S, 8.15. Found: C, 63.90; H, 4.17; N, 10.69; S, 8.07.

EXAMPLE 17

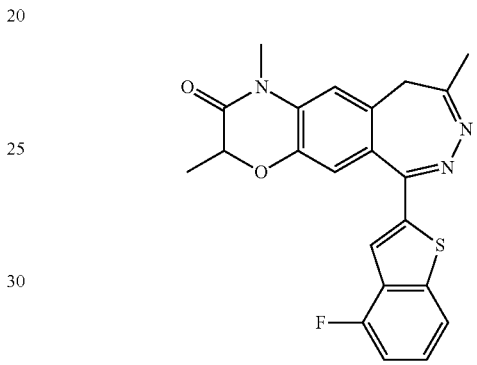

6-(4-Fluoro-1-benzo[b]thiophen-2-yl)-1,3,9-trimethyl-1,10-dihydro[1,4]oxazino[3,2-h][2,3]benzodiazepin-2(3H)-one The preparation of the title compound is analogous with the method described in Example 1. The last step of the synthesis was N-alkylation in position 1, it was performed as follows: The mixture of 6-(4-fluoro-1-benzothiophen-2-yl)-3,9-dimethyl-1,10-dihydro[1,4]oxazino[3,2-h][2,3]benzodiazepin-2(3H)-one (0.85 g, 2.2 mmol), K$_2$CO$_3$ (0.85 g, 6.2 mmol), methyl iodide (0.14 mL, 2.3 mmol) and acetone (25.5 mL) was stirred for 4 days at room temperature. The reaction mixture was then filtered, washed with acetone (3×10 mL), and the product was purified by flash chromatography (0.45 g, 51%).

Mp: 210-212° C. IR (KBr, cm$^{-1}$): 1695, 1508, 1467, 1374, 773. $^1$H NMR (DMSO-d$_6$, 500 MHz): δ 7.85 (m, 1H), 7.46-7.41 (d, J=0.6 Hz, 1H), 7.45 (m, 1H), 7.39-7.38 (s, 1H), 7.37-7.34 (s, 1H), 7.21 (m, 1H), 4.91-4.78 (q, J=6.8 Hz, 1H), 3.56 (d, J=12.3 Hz, 1H), 2.90-2.87 (d, J=12.1 Hz, 1H), 2.11-2.10 (s, 3H), 1.51-1.46 (d, J=6.7 Hz, 3H) ppm. $^{13}$C NMR (DMSO-d$_6$, 125 MHz): 166.61, 166.48, 157.28 (d, J=251.0 Hz), 155.65, 155.64, 151.84, 151.77, 144.59, 144.37, 143.41, 143.28, 142.26 (d, J=5.4 Hz), 134.84, 134.75, 133.57, 133.44, 128.43 (d, J=19.0 Hz), 127.34 (d, J=7.3 Hz), 122.44 (d, J=1.5 Hz), 120.71, 119.06, 116.43, 113.83, 113.62, 109.92 (d, J=18.1 Hz), 73.04, 72.97, 37.47, 28.74, 28.61, 22.80, 22.77, 16.58, 16.39 ppm. Elementary analysis calculated: C, 64.85; H, 4.45; F, 4.66; N, 10.31; S, 7.87. Found: C, 64.89; H, 4.59; N, 10.21; S, 7.83.

EXAMPLE 18

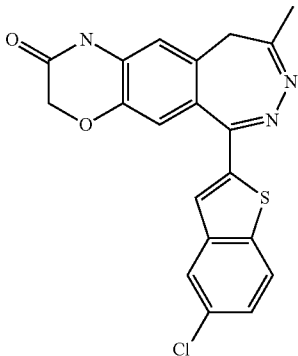 [SMILES: CC1=NN=C(c2cc3cc(Cl)ccc3s2)c2cc3c(cc2C1)NC(=O)CO3]

6-(5-Chloro-1-benzo[b]thiophen-2-yl)-9-methyl-1,
10-dihydro[1,4]oxazino[3,2-h][2,3]benzodiazepin-2
(3H)-one The preparation of the title compound is analogous with the method described in Example 1. Mp: 297-300° C. IR (KBr, cm$^{-1}$): 2949, 1704, 1505, 1024, 811. $^1$H NMR (DMSO-d$_6$, 500 MHz): δ 11.12 (br s, 1H), 8.02 (d, J=8.6 Hz, 1H), 7.98 (d, J=2.1 Hz, 1H), 7.51 (s, 1H), 7.43 (dd, J$_1$=2.1 Hz, J$_2$=8.5 Hz, 1H), 7.30 (s, 1H), 6.95 (s, 1H), 4.66 (s, 2H), 3.46 (d, J=12.5 Hz, 1H), 2.84 (d, J=12.3 Hz, 1H), 2.06 (s, 3H) ppm. $^{13}$C NMR (DMSO-d$_6$, 125 MHz): 165.21, 155.45, 151.96, 145.60, 142.49, 141.13, 138.40, 134.49, 131.23, 129.69, 126.39, 125.94, 124.27, 124.12, 122.40, 116.58, 113.58, 66.88, 37.29, 22.70. Elementary analysis calculated: C, 60.68; H, 3.56; Cl, 8.96; N, 10.61; S, 8.10. Found: C, 60.54; H, 3.69; Cl, 8.88; N, 10.56; S, 7.98.

EXAMPLE 19

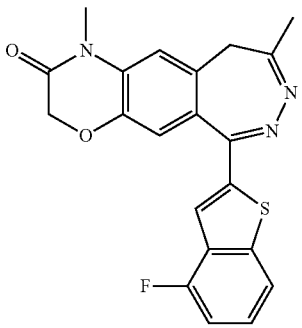 [SMILES: CC1=NN=C(c2cc3c(F)cccc3s2)c2cc3c(cc2C1)N(C)C(=O)CO3]

6-(4-Fluoro-1-benzo[b]thiophen-2-yl)-1,9-dimethyl-
1,10-dihydro[1,4]oxazino[3,2-h][2,3]benzodiazepin-
2(3H)-one The preparation of the title compound is analogous with the method described in Example 1.
The last step of the synthesis was N-alkylation in position 1, performed analogously with the method described in Example 17.

Mp: 216-218° C. IR (KBr, cm$^{-1}$): 1697, 1606, 1383, 794. $^1$H NMR (DMSO-d$_6$, 500 MHz): δ 7.87 (m, 1H), 7.45 (m, 1H), 7.43 (d, J=0.6 Hz, 1H), 7.39 (s, 1H), 7.36 (s, 1H), 7.21 (m, 1H), 4.78 (d, J=15.1 Hz, 1H), 4.72 (d, J=15.0 Hz, 1H), 3.55 (d, J=12.3 Hz, 1H), 3.36 (s, 3H), 2.88 (d, J=12.2 Hz, 1H), 2.10 (s, 3H) ppm. Elementary analysis calculated: C, 64.11; H, 4.10; F, 4.83; N, 10.68; S, 8.15. Found: C, 63.86; H, 4.24; N, 10.64; S, 8.00.

EXAMPLE 20

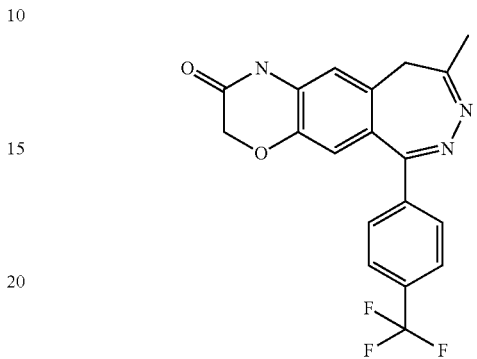

6-(4-Trifluoromethyl-phenyl)-9-methyl-1,10-dihydro
[1,4]oxazino[3,2-h][2,3]benzodiazepin-2(3H)-one The preparation of the title compound is analogous with the method described in Example 1. Mp: 295-298° C. IR (KBr, cm$^{-1}$): 3055, 1709, 1323, 1128. $^1$H NMR (DMSO-d$_6$, 500 MHz): δ 11.10 (br s, 1H), 7.82 (~d, J=8.4 Hz, 2H), 7.77 (~d, J=8.6 Hz, 2H), 6.95 (s, 1H), 6.79 (s, 1H), 4.61 (d, J=15.1 Hz, 1H), 4.59 (d, J=15.3 Hz, 1H), 3.48 (d, J=12.5 Hz, 1H), 2.82 (d, J=12.3 Hz, 1H), 2.06 (s, 3H) ppm. $^{13}$C NMR (DMSO-d$_6$, 125 MHz): 165.20, 155.94, 154.93, 142.48, 142.30, 134.87, 130.97, 129.89 (q, J=31.7 Hz), 129.89, 125.40 (q, J=3.7 Hz), 124.33 (q, J=269.3 Hz), 123.76, 116.55, 113.43, 66.85, 37.32, 22.65 ppm. Elementary analysis calculated: C, 61.13; H, 3.78; F, 15.27; N, 11.26. Found: C, 60.75; H, 3.85; N, 11.34.

EXAMPLE 21

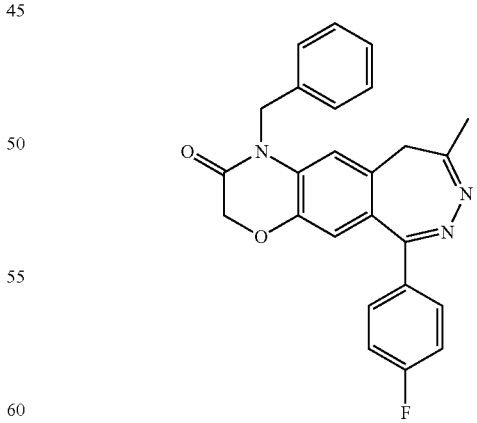

1-Benzyl-6-(4-fluorophenyl)-9-methyl-1,10-dihydro
[1,4]oxazino[3,2-h][2,3]benzodiazepin-2(3H)-one The preparation of the title compound is analogous with the method described in Example 1.

The last step of the synthesis was N-alkylation in position 1, performed analogously with the method described in Example 17.

Mp: 258-261° C. IR (KBr, cm$^{-1}$): 3441, 1702, 1509, 1390. $^1$H NMR (DMSO-d$_6$, 500 MHz): δ 7.59 (~dd, J$_1$=5.6 Hz, J$_2$=8.9 Hz, 2H), 7.36 (m, 4H), 7.27 (m, 3H), 7.23 (s, 1H), 6.81 (s, 1H), 5.27 (d, J=16.0 Hz, 1H), 5.22 (d, J=16.1 Hz, 1H), 4.83 (d, J=15.0 Hz, 1H), 4.81 (d, J=15.0 Hz, 1H), 3.38 (d, J=12.1 Hz, 1H), 2.77 (d, J=12.1 Hz, 1H), 1.93 (s, 3H) ppm. $^{13}$C NMR (DMSO-d$_6$, 125 MHz): 164.55, 163.28 (d, J=247.6 Hz), 155.48, 154.68, 143.86, 136.25, 134.86 (d, J=2.9 Hz), 134.47, 131.56, 131.31 (d, J=8.8 Hz), 128.79, 127.47, 127.17, 124.29, 116.74, 115.45 (d, J=22.0 Hz), 113.83, 67.17, 43.60, 37.38, 22.42 ppm. Elementary analysis calculated: C, 72.63; H, 4.88; F, 4.60; N, 10.16. Found: C, 72.05; H, 5.11; N, 9.88.

EXAMPLE 22

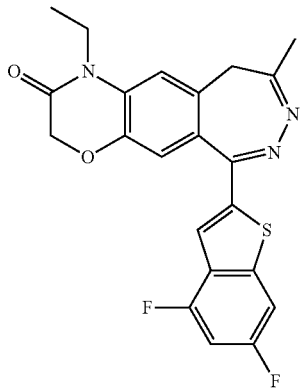 [SMILES: CCN1C(=O)COc2cc3c(cc21)CC(C)=NN=C3c1cc2c(F)cc(F)cc2s1]

6-(4,6-Difluoro-1-benzothiophen-2-yl)-1-ethyl-9-methyl-1,10-dihydro[1,4]oxazino[3,2-h][2,3]benzodiazepin-2(3H)-one The preparation of the title compound is analogous with the method described in Example 1. The last step of the synthesis was N-alkylation in position 1, performed analogously with the method described in Example 17.

Mp: 168-170° C. IR (KBr, cm$^{-1}$): 1699, 1422, 1390, 1284. $^1$H NMR (DMSO-d$_6$, 500 MHz): δ 7.85 (dd, J$_1$=1.7 Hz, J$_2$=8.7 Hz, 1H), 7.42 (s, 2H), 7.38 (s, 1H), 7.32 (~dt, J$_1$=2.1 Hz, J$_2$=10.0 Hz), 4.76 (d, J=15.0 Hz, 1H), 4.70 (d, J=15.1 Hz, 1H), 4.01 (m, 2H), 3.60 (d, J=12.3 Hz, 1H), 2.87 (d, J=12.2 Hz, 1H), 2.10 (s, 3H), 1.23 (t, J=7.1 Hz, 3H) ppm. Elementary analysis calculated: C, 62.11; H, 4.03; F, 8.93; N, 9.88; S, 7.54. Found: C, 61.62; H, 4.19; N, 9.61; S, 7.63.

EXAMPLE 23

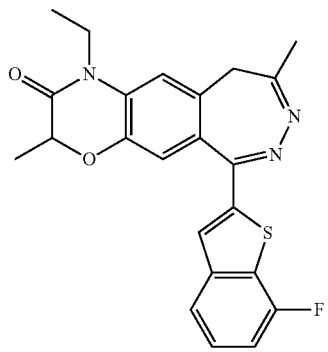 [SMILES: CCN1C(=O)C(C)Oc2cc3c(cc21)CC(C)=NN=C3c1cc2cccc(F)c2s1]

Ethyl-6-(7-fluoro-1-benzothiophen-2-yl)-3,9-dimethyl-1,10-dihydro[1,4]oxazino[3,2-h][2,3]benzodiazepin-2(3H)-one The preparation of the title compound is analogous with the method described in Example 1. The last step of the synthesis was N-alkylation in position 1, performed analogously with the method described in Example 17.

Mp: 190-192° C. IR (KBr, cm$^{-1}$): 3442, 1683, 1466, 1427. $^1$H NMR (DMSO-d$_6$, 500 MHz): δ 7.76 (m, 2H), 7.63-7.65 (d, J=3.5 Hz, 1H), 7.49-7.48 (s, 1H), 7.42 (m, 1H), 7.37 (s, 1H), 7.29 (m, 1H), 4.76-4.82 (q, J=6.6 Hz, 1H), 4.01 (m, 2H), 3.60 (d, J=12.2 Hz, 1H), 2.90-2.88 (d, J=12.3 Hz, 1H), 2.10-2.12 (s, 3H), 1.50-1.45 (d, J=6.6 Hz, 3H), 1.22 (t, J=7.0 Hz, 3H) ppm. $^{13}$C NMR (DMSO-d$_6$, 125 MHz): 166.07, 165.88, 156.73 (d, J=239.7 Hz), 155.74, 151.72, 151.65, 144.67, 144.46, 143.53 (d, J=22.5 Hz), 143.35 (d, J=22.9 Hz), 134.87, 134.84, 132.32, 132.20, 127.48, 127.35, 126.54 (d, J=5.9 Hz), 126.23, 122.46, 122.44, 121.40, 121.36, 116.90 (d, J=4.4 Hz), 113.31 (d, J=19.0 Hz), 111.14 (d, J=18.6 Hz), 72.96, 72.84, 37.38, 36.47, 36.37, 22.97, 22.79, 22.74, 16.40, 16.29, 12.56, 12.50 ppm. Elementary analysis calculated: C, 65.54; H, 4.78; F, 4.51; N, 9.97; S, 7.61. Found: C, 64.86; H, 4.97; N, 9.50; S, 7.84.

EXAMPLE 24

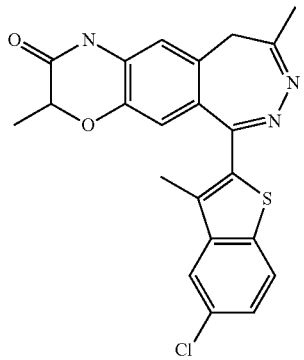

6-(5-Chloro-3-methyl-1-benzothiophen-2-yl)-3,9-dimethyl-1,10-dihydro[1,4]oxazino[3,2-h][2,3]benzodiazepin-2(3H)-one The preparation of the title compound is analogous with the method described in Example 1.

Mp: 286-290° C. IR (KBr, cm$^{-1}$): 3442, 1686, 1501, 1291. $^1$H NMR (DMSO-d$_6$, 500 MHz): δ 11.09 (br s, 1H), 8.03 (d, J=8.6 Hz, 1H), 7.88-7.87 (s, 1H), 7.46 (d, J=8.4 Hz, 1H), 6.97-6.96 (s, 1H), 6.85-6.83 (s, 1H), 4.73-4.68 (q, J=6.8 Hz, 1H), 3.54 (d, J=12.3 Hz, 1H), 2.86-2.85 (d, J=12.3 Hz, 1H), 2.08 (s, 3H), 2.05-2.00 (s, 3H), 1.41-1.37 (d, J=6.7 Hz, 3H) ppm. $^{13}$C NMR (DMSO-d$_6$, 125 MHz): 167.49, 167.25, 154.87, 154.83, 152.52, 152.42, 142.49, 142.29, 142.22, 142.18, 138.40, 138.37, 137.50, 137.49, 133.84, 133.73, 132.08, 131.71, 129.79, 129.76, 125.74, 124.51, 124.32, 124.27, 122.25, 116.66, 113.16, 72.95, 72.79, 37.25, 22.79, 22.77, 16.33, 15.98, 13.81, 13.74 ppm. Elementary analysis calculated: C, 62.33; H, 4.28; Cl, 8.36; N, 9.91; S, 7.56. Found: C, 60.37; H, 4.37; Cl, 9.08; N, 9.86; S, 7.44.

EXAMPLE 25

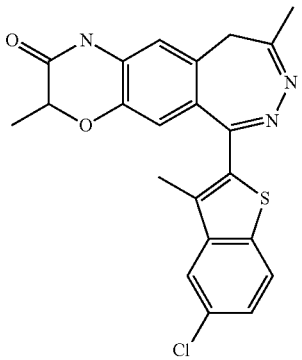 [SMILES: CC1=NN=C(c2sc3ccc(Cl)cc3c2C)c2cc3c(cc2C1)NC(=O)C(C)O3]

(+)-6-(5-Chloro-3-methyl-1-benzothiophen-2-yl)-3,9-dimethyl-1,10-dihydro[1,4]oxazino[3,2-h][2,3]benzodiazepin-2(3H)-one The preparation of the title compound is analogous with the method described in Example 1.

The chiral chromatographic conditions were analogous with the method described in Examples 3 and 4.

Mp: 298-314° C. $[\alpha]_D$=+24.1° (c=1, DMSO). IR (KBr, cm$^{-1}$): 3442, 1686, 1501, 1291. $^1$H NMR (DMSO-d$_6$, 500 MHz): δ 11.09 (br s, 1H), 8.03 (d, J=8.6 Hz, 1H), 7.88-7.87 (s, 1H), 7.46 (d, J=8.4 Hz, 1H), 6.97-6.96 (s, 1H), 6.85-6.83 (s, 1H), 4.73-4.68 (q, J=6.8 Hz, 1H), 3.54 (d, J=12.3 Hz, 1H), 2.86-2.85 (d, J=12.3 Hz, 1H), 2.08 (s, 3H), 2.05-2.00 (s, 3H), 1.41-1.37 (d, J=6.7 Hz, 3H) ppm. $^{13}$C NMR (DMSO-d$_6$, 125 MHz): 167.49, 167.25, 154.87, 154.83, 152.52, 152.42, 142.49, 142.29, 142.22, 142.18, 138.40, 138.37, 137.50, 137.49, 133.84, 133.73, 132.08, 131.71, 129.79, 129.76, 125.74, 124.51, 124.32, 124.27, 122.25, 116.66, 113.16, 72.95, 72.79, 37.25, 22.79, 22.77, 16.33, 15.98, 13.81, 13.74 ppm. Elementary analysis calculated: C, 62.33; H, 4.28; Cl, 8.36; N, 9.91; S, 7.56. Found: C, 61.64; H, 4.40; Cl, 8.49; N, 9.86; S, 7.49.

EXAMPLE 26

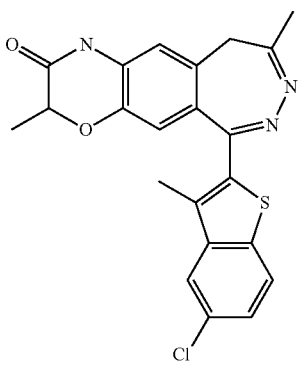 [SMILES: CC1=NN=C(c2sc3ccc(Cl)cc3c2C)c2cc3c(cc2C1)NC(=O)C(C)O3]

(−)-6-(5-Chloro-3-methyl-1-benzothiophen-2-yl)-3,9-dimethyl-1,10-dihydro[1,4]oxazino[3,2-h][2,3]benzodiazepin-2(3H)-one The preparation of the title compound is analogous with the method described in Example 1.

The chiral chromatographic conditions were analogous with the method described in Examples 3 and 4.

Mp: 302-310° C. $[\alpha]_D$=−22.5° (c=1, DMSO). IR, $^1$H NMR and $^{13}$C NMR data are identical with those described for the other enantiomer in Example 25. Elementary analysis calculated: C, 62.33; H, 4.28; Cl, 8.36; N, 9.91; S, 7.56. Found: C, 60.62; H, 4.55; Cl, 8.23; N, 9.77; S, 7.32.

EXAMPLE 27

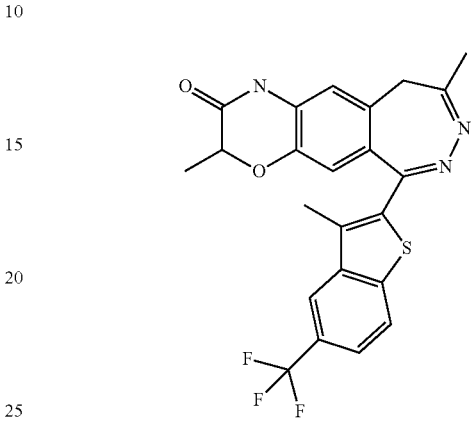

3,9-Dimethyl-6-[3-methyl-5-(trifluoromethyl)-1-benzothiophen-2-yl]-1,10-dihydro[1,4]oxazino[3,2-h][2,3]benzodiazepin-2(3H)-one The preparation of the title compound is analogous with the method described in Example 1.

Mp: 288-290° C. IR (KBr, cm$^{-1}$): 3050, 1705, 1330, 1122. $^1$H NMR (DMSO-d$_6$, 500 MHz): δ 11.07 (br s, 1H), 8.25 (d, J=8.4 Hz, 1H), 8.16-8.15 (s, 1H), 7.73 (d, J=8.6 Hz, 1H), 6.98-6.96 (s, 1H), 6.88-6.86 (s, 1H, 4.73-4.68 (q, =6.8 Hz, 1H), 3.55 (d, J=12.5 Hz, 1H), 2.87 (d, 1H), 2.09-2.07 (s, 3H), 1.41-1.37 (d, J=6.8 Hz, 3H) ppm. Elementary analysis calculated: C, 60.39; H, 3.97; F, 12.46; N, 9.19; S, 7.01. Found: C, 58.61; H, 3.86; N, 8.96; S, 6.91.

EXAMPLE 28

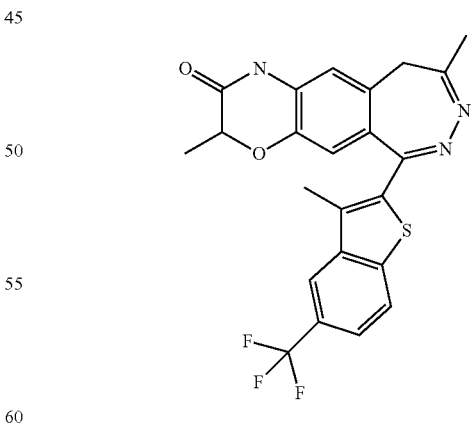

(+)-3,9-Dimethyl-6-[3-methyl-5-(trifluoromethyl)-1-benzothiophen-2-yl]-1,10-dihydro[1,4]oxazino[3,2-h][2,3]benzodiazepin-2(3H)-one The preparation of the title compound is analogous with the method described in Example 1.

The chiral chromatographic conditions were analogous with the method described in Examples 3 and 4.

Mp: 287-289° C. [α]$_D$=+25.0° (c=0.5, DMSO). IR (KBr, cm$^{-1}$): 3174, 1711, 1374, 1331, 1299, 1119. $^1$H NMR (DMSO-d$_6$, 500 MHz): δ 11.07 (br s, 1H), 8.25 (d, J=8.4 Hz, 1H), 8.16-8.15 (s, 1H), 7.73 (d, J=8.6 Hz, 1H), 6.98-6.96 (s, 1H), 6.88-6.86 (s, 1H), 4.73-4.68 (q, =6.8 Hz, 1H), 3.55 (d, J=12.5 Hz, 1H), 2.87 (d, 1H), 2.09-2.07 (s, 3H), 1.41-1.37 (d, J=6.8 Hz, 3H) ppm. Elementary analysis calculated: C, 60.39; H, 3.97; F, 12.46; N, 9.19; S, 7.01. Found: C, 59.93; H, 3.99; N, 9.17; S, 7.19.

EXAMPLE 29

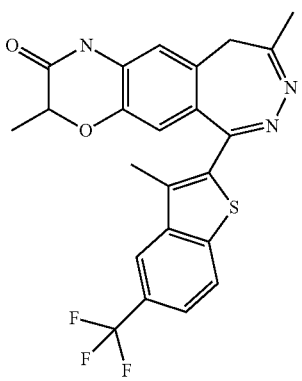 [SMILES: CC1=NN=C(c2sc3ccc(C(F)(F)F)cc3c2C)c2cc3c(cc2C1)NC(=O)C(C)O3]

(−)-3,9-Dimethyl-6-[3-methyl-5-(trifluoromethyl)-1-benzothiophen-2-yl]-1,10-dihydro[1,4]oxazino[3,2-h][2,3]benzodiazepin-2(3H)-one The preparation of the title compound is analogous with the method described in Example 1.

The chiral chromatographic conditions were analogous with the method described in Examples 3 and 4.

Mp: 290-292° C. [α]$_D$=−22.4° (c=0.5, DMSO). IR, $^1$H NMR and $^{13}$C NMR data are identical with those described for the other enantiomer in Example 29. Elementary analysis calculated: C, 60.39; H, 3.97; F, 12.46; N, 9.19; S, 7.01. Found: C, 59.79; H, 3.93; N, 9.16; S, 7.21.

EXAMPLE 30

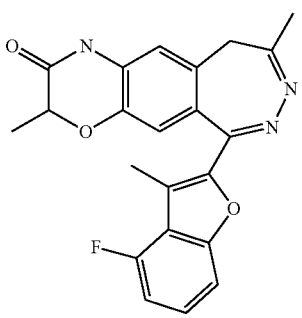 [SMILES: CC1=NN=C(c2oc3cccc(F)c3c2C)c2cc3c(cc2C1)NC(=O)C(C)O3]

6-(4-Fluoro-3-methyl-1-benzofuran-2-yl)-3,9-dimethyl-1,10-dihydro[1,4]oxazino[3,2-h][2,3]benzodiazepin-2(3H)-one The preparation of the title compound is analogous with the method described in Example 2.

Mp: 276-283° C. IR (KBr, cm$^{-1}$): 3193, 1690, 1510, 1392, 1314, 1045, 1036. $^1$H NMR (DMSO-d$_6$, 500 MHz): δ 11.01 (br s, 1H), 7.41 (m, 1H), 7.37 (m, 1H), 7.10 (m, 1H), 6.94-6.93 (s, 1H), 6.93-6.91 (s, 1H), 4.77-4.68 (q, J=6.8 Hz, 1H), 3.51 (d, J=12.5 Hz, 1H), 2.83 (d, J=12.3 Hz, 1H), 2.48 (s, 3H), 2.09 (s, 3H), 1.44-1.38 (d, J=6.6 Hz, 3H) ppm. $^{13}$C NMR (DMSO-d$_6$, 125 MHz): 167.42, 167.19, 156.71 (d, J=250.0 Hz), 155.39 (d, J=9.8 Hz), 154.77, 154.74, 148.96, 148.90, 148.21, 142.34, 141.88, 134.12 (d, J=19.0 Hz), 131.57, 126.60 (d, J=8.3 Hz), 123.11, 122.97, 118.51, 116.77, 116.72, 115.42, 113.05, 112.96, 108.83 (d, J=16.1 Hz), 108.23 (d, J=3.4 Hz), 72.86, 72.75, 37.24, 22.66, 22.65, 16.32, 15.99, 10.91 ppm. Elementary analysis calculated: C, 67.51; H, 4.64; F, 4.85; N, 10.74. Found: C, 66.69; H, 4.85; N, 10.65.

EXAMPLE 31

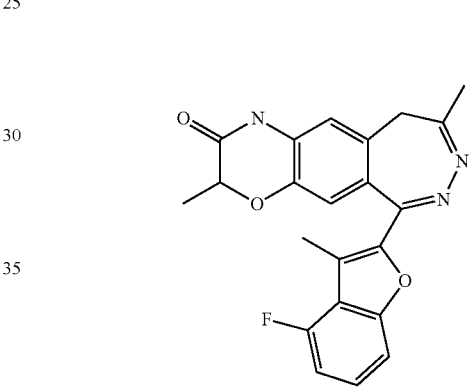

(−)-6-(4-Fluoro-3-methyl-1-benzofuran-2-yl)-3,9-dimethyl-1,10-dihydro[1,4]oxazino[3,2-h][2,3]benzodiazepin-2(3H)-one The preparation of the title compound is analogous with the method described in Example 2.

The chiral chromatographic conditions were analogous with the method described in Examples 3 and 4.

Mp: 284-288° C. [α]$_D$=−20.0° (c=0.5, IPA-MeOH-DMSO 1:1:1). IR (KBr, cm$^{-1}$): 3193, 1690, 1510, 1392, 1314, 1045, 1036. $^1$H NMR (DMSO-d$_6$, 500 MHz): δ 11.01 (br s, 1H), 7.41 (m, 1H), 7.37 (m, 1H), 7.10 (m, 1H), 6.94-6.93 (s, 1H), 6.93-6.91 (s, 1H), 4.77-4.68 (q, J=6.8 Hz, 1H), 3.51 (d, J=12.5 Hz, 1H), 2.83 (d, J=12.3 Hz, 1H), 2.48 (s, 3H), 2.09 (s, 3H), 1.44-1.38 (d, J=6.6 Hz, 3H) ppm. $^{13}$C NMR (DMSO-d$_6$, 125 MHz): 167.42, 167.19, 156.71 (d, J=250.0 Hz), 155.39 (d, J=9.8 Hz), 154.77, 154.74, 148.96, 148.90, 148.21, 142.34, 141.88, 134.12 (d, J=19.0 Hz), 131.57, 126.60 (d, J=8.3 Hz), 123.11, 122.97, 118.51, 116.77, 116.72, 115.42, 113.05, 112.96, 108.83 (d, J=16.1 Hz), 108.23 (d, J=3.4 Hz), 72.86, 72.75, 37.24, 22.66, 22.65, 16.32, 15.99, 10.91 ppm. Elementary analysis calculated: C, 67.51; H, 4.64; F, 4.85; N, 10.74. Found: C, 67.41; H, 4.76; N, 10.86.

EXAMPLE 32

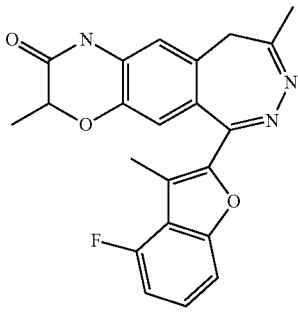 [SMILES: CC1=NN=C(c2oc3cccc(F)c3c2C)c2cc3c(cc2C1)NC(=O)C(C)O3]

(+)-6-(4-Fluoro-3-methyl-1-benzofuran-2-yl)-3,9-dimethyl-1,10-dihydro[1,4]oxazino[3,2-h][2,3]benzodiazepin-2(3H)-one The preparation of the title compound is analogous with the method described in Example 2.

The chiral chromatographic conditions were analogous with the method described in Examples 3 and 4.

Mp: 283-285° C. [α]$_D$=+21.8° (c=0.5, IPA-MeOH-DMSO 1:1:1). IR, $^1$H NMR and $^{13}$C NMR data are identical with those described for the other enantiomer in Example 32. Elementary analysis calculated: C, 67.51; H, 4.64; F, 4.85; N, 10.74. Found: C, 67.48; H, 4.78; N, 10.89.

EXAMPLE 33

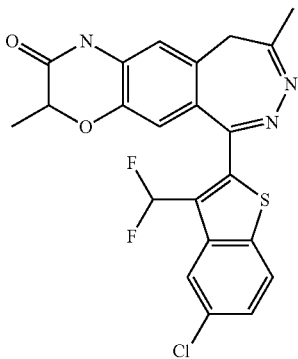 [SMILES: CC1=NN=C(c2sc3ccc(Cl)cc3c2C(F)F)c2cc3c(cc2C1)NC(=O)C(C)O3]

6-[5-Chloro-3-(difluoromethyl)-1-benzothiophen-2-yl]-3,9-dimethyl-1,10-dihydro[1,4]oxazino[3,2-h][2,3]benzodiazepin-2(3H)-one The preparation of the title compound is analogous with the method described in Example 1.

Mp: 242-245° C. IR (KBr, cm$^{-1}$): 3056, 1692, 1508, 1390, 1302, 1087. $^1$H NMR (DMSO-d$_6$, 500 MHz): δ 11.10 (br s, 1H), 8.16 (m, 1H), 8.01 (m, 1H), 7.59-7.57 (m, 1H), 7.16-7.01 (t, J=53.8 Hz, 1H), 7.00-6.99 (s, 1H), 6.96 (s, 1H), 4.73-4.69 (q, J=4.8 Hz, 1H), 3.57 (d, J=12.5 Hz, 1H), 2.93-2.90 (d, 1H), 2.10-2.09 (s, 3H), 1.41-1.37 (d, J=6.8 Hz, 3H) ppm. $^{13}$C NMR (DMSO-d$_6$, 125 MHz): 167.40, 167.15, 155.31, 155.26, 150.55, 150.44, 146.52, 142.07, 141.74, 137.90, 137.87, 137.46, 137.40, 134.44, 134.37, 132.20, 132.19, 130.70, 130.68, 126.95-126.88 (t, J=25.4 Hz), 126.39, 124.95, 124.25, 124.17, 122.78, 117.00, 116.92, 113.25, 113.16, 111.71-111.61 (t, J=233.9 Hz), 72.91, 72.77, 37.53, 22.64, 22.60, 16.31, 15.99 ppm. Elementary analysis calculated: C, 57.46; H, 3.51; Cl, 7.71; F, 8.26; N, 9.14; S, 6.97. Found: C, 57.44; H, 3.53; Cl, 7.73; N, 9.12; S, 6.94.

EXAMPLE 34

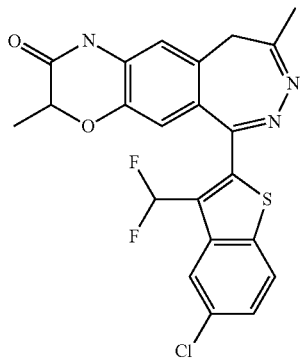 [SMILES: CC1=NN=C(c2sc3ccc(Cl)cc3c2C(F)F)c2cc3c(cc2C1)NC(=O)C(C)O3]

(−)-6-[5-Chloro-3-(difluoromethyl)-1-benzothiophen-2-yl]-3,9-dimethyl-1,10-dihydro[1,4]oxazino[3,2-h][2,3]benzodiazepin-2(3H)-one The preparation of the title compound is analogous with the method described in Example 1.

The chiral chromatographic conditions were analogous with the method described in Examples 3 and 4.

Mp: 213-215° C. [α]$_D$=−24.0° (c=0.5, MeOH—CHCl$_3$ 1:1). IR (KBr, cm$^{-1}$): 3056, 1692, 1508, 1390, 1302, 1087. $^1$H NMR (DMSO-d$_6$, 500 MHz): δ 11.10 (br s, 1H), 8.16 (m, 1H), 8.01 (m, 1H), 7.59-7.57 (m, 1H), 7.16-7.01 (t, J=53.8 Hz, 1H), 7.00-6.99 (s, 1H), 6.96 (s, 1H), 4.73-4.69 (q, J=4.8 Hz, 1H), 3.57 (d, J=12.5 Hz, 1H), 2.93-2.90 (d, 1H), 2.10-2.09 (s, 3H), 1.41-1.37 (d, J=6.8 Hz, 3H) ppm. $^{13}$C NMR (DMSO-d$_6$, 125 MHz): 167.40, 167.15, 155.31, 155.26, 150.55, 150.44, 146.52, 142.07, 141.74, 137.90, 137.87, 137.46, 137.40, 134.44, 134.37, 132.20, 132.19, 130.70, 130.68, 126.95-126.88 (t, J=25.4 Hz), 126.39, 124.95, 124.25, 124.17, 122.78, 117.00, 116.92, 113.25, 113.16, 111.71-111.61 (t, J=233.9 Hz), 72.91, 72.77, 37.53, 22.64, 22.60, 16.31, 15.99 ppm. Elementary analysis calculated: C, 57.46; H, 3.51; Cl, 7.71; F, 8.26; N, 9.14; S, 6.97. Found: C, 57.10; H, 3.56; Cl, 7.87; N, 9.14; S, 7.04.

EXAMPLE 35

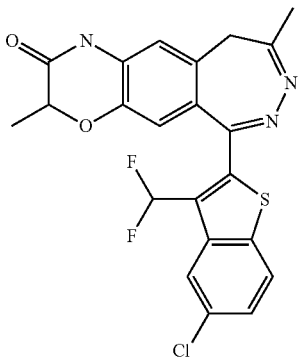 [SMILES: CC1=NN=C(c2sc3ccc(Cl)cc3c2C(F)F)c2cc3c(cc2C1)NC(=O)C(C)O3]

(+)-6-[5-Chloro-3-(difluoromethyl)-1-benzothiophen-2-yl]-3,9-dimethyl-1,10-dihydro[1,4]oxazino[3,2-h][2,3]benzodiazepin-2(3H)-one The preparation of the title compound is analogous with the method described in Example 1.
The chiral chromatographic conditions were analogous with the method described in Examples 3 and 4.
Mp: 185-187° C. $[\alpha]_D=+19.6°$ (c=0.5, MeOH—CHCl$_3$ 1:1). IR, $^1$H NMR and $^{13}$C NMR data are identical with those described for the other enantiomer in Example 35. Elementary analysis calculated: C, 57.46; H, 3.51; Cl, 7.71; F, 8.26; N, 9.14; S, 6.97. Found: C, 56.99; H, 3.54; Cl, 7.45; N, 8.66; S, 6.58.

EXAMPLE 36

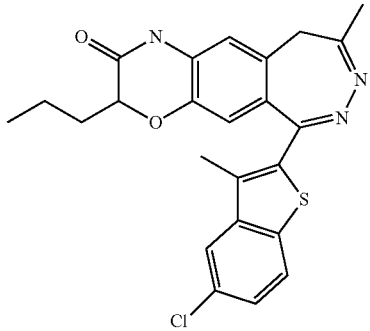 [SMILES: CCCC1Oc2cc3c(cc2NC1=O)CC(C)=NN=C3c1sc2ccc(Cl)cc2c1C]

(+)-6-(5-Chloro-3-methyl-1-benzothiophen-2-yl)-9-methyl-3-propyl-1,10-dihydro[1,4]oxazino[3,2-h][2,3]benzodiazepin-2(3H)-one The preparation of the title compound is analogous with the method described in Example 1.
The chiral chromatographic conditions were analogous with the method described in Examples 3 and 4.
Mp: 259-268° C. $[\alpha]_D=+37.5°$ (c=0.5, DMSO). IR (KBr, cm$^{-1}$): 3045, 1706, 1506, 1352, 1290. $^1$H NMR (DMSO-d$_6$, 400 MHz): δ 11.07 (br s, 1H), 8.02 (d, J=8.5 Hz, 1H), 7.87 (s, 1H), 7.46 (d, J=8.5 Hz, 1H), 6.96-6.94 (s, 1H), 6.86-6.85 (s, 1H), 4.60 (m, 1H), 3.54 (d, J=12.3 Hz, 1H), 2.87 (d, J=12.4 Hz, 1H), 2.09-2.08 (s, 3H), 2.04-2.00 (s, 3H), 1.70 (m, 2H), 1.42 (m, 2H), 0.90-0.83 (m, 3H) ppm. $^{13}$C NMR (DMSO-d$_6$, 100 MHz): 167.01, 166.77, 154.74, 152.38, 142.27, 142.20, 142.13, 141.57, 138.47, 138.38, 137.47, 133.71, 133.52, 131.99, 131.95, 131.55, 131.27, 129.75, 125.71, 124.52, 124.29, 124.21, 122.16, 116.72, 113.03, 112.96, 76.10, 75.92, 37.23, 32.11, 31.89, 22.73, 22.70, 17.69, 13.69, 13.64, 13.60, 13.49 ppm. Elementary analysis calculated: C, 63.78; H, 4.91; Cl, 7.84; N, 9.30; S, 7.09. Found: C, 62.80; H, 5.16; Cl, 7.89; N, 9.27; S, 7.19.

EXAMPLE 37

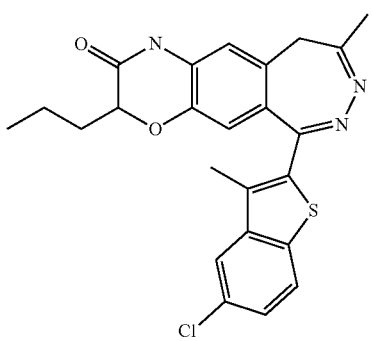 [SMILES: CCCC1Oc2cc3c(cc2NC1=O)CC(C)=NN=C3c1sc2ccc(Cl)cc2c1C]

(−)-6-(5-Chloro-3-methyl-1-benzothiophen-2-yl)-9-methyl-3-propyl-1,10-dihydro[1,4]oxazino[3,2-h][2,3]benzodiazepin-2(3H)-one The preparation of the title compound is analogous with the method described in Example 1.
The chiral chromatographic conditions were analogous with the method described in Examples 3 and 4.
Mp: 265-272° C. $[\alpha]_D=-38.5°$ (c=0.5, DMSO). IR, $^1$H NMR and $^{13}$C NMR data are identical with those described for the other enantiomer in Example 37. Elementary analysis calculated: C, 63.78; H, 4.91; Cl, 7.84; N, 9.30; S, 7.09. Found: C, 62.30; H, 5.07; Cl, 7.79; N, 9.16; S, 7.21.

EXAMPLE 38

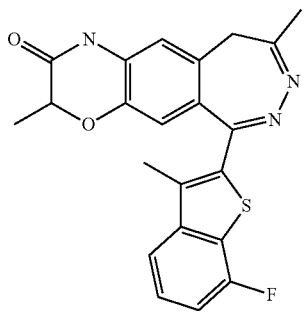 [SMILES: CC1=NN=C(c2sc3c(F)cccc3c2C)c2cc3c(cc2C1)NC(=O)C(C)O3]

(+)-6-(7-Fluoro-3-methyl-1-benzothiophen-2-yl)-3,9-dimethyl-1,10-dihydro[1,4]oxazino[3,2-h][2,3]benzodiazepin-2(3H)-one The preparation of the title compound is analogous with the method described in Example 1.

The chiral chromatographic conditions were analogous with the method described in Examples 3 and 4.

Mp: 282-285° C. $[\alpha]_D$=+28.0° (c=0.5, DMSO). IR (KBr, cm$^{-1}$): 3196, 3117, 1699, 1506, 1306, 784. $^1$H NMR (DMSO-d$_6$, 500 MHz): δ 11.07 (br s, 1H), 7.69-7.68 (m, 1H), 7.48 (m, 1H), 7.32 (m, 1H), 6.98-6.97 (s, 1H), 6.89-6.87 (s, 1H), 4.73-4.69 (q, J=6.8 Hz, 1H), 3.56 (d, J=12.5 Hz, 1H), 2.88 (d, J=12.5 Hz, 1H), 2.09 (s, 3H), 2.07-2.02 (s, 3H), 1.42-1.37 (d, J=6.8 Hz, 3H) ppm. $^{13}$C NMR (DMSO-d$_6$, 125 MHz): 167.44, 167.22, 156.74 (d, J=244.1 Hz), 154.90, 154.86, 152.36, 152.27, 144.41 (d, J=7.8 Hz), 144.41, 144.35, 142.50, 142.22, 137.28, 133.80, 133.69, 133.08, 131.76, 131.75, 126.37, 126.36 (d, J=10.7 Hz), 125.36 (d, J=18.6 Hz), 124.30, 124.12, 119.22 (d, J=2.9 Hz), 116.61, 113.15, 113.04, 110.94 (d, J=18.1 Hz), 72.92, 72.77, 37.25, 22.74, 22.72, 16.30, 15.95, 14.11, 14.06 ppm. Elementary analysis calculated: C, 64.85; H, 4.45; F, 4.66; N, 10.31; S, 7.87. Found: C, 64.30; H, 4.56; N, 10.26; S, 7.65.

EXAMPLE 39

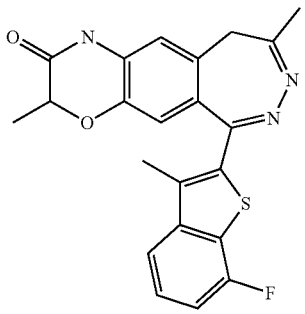 [SMILES: CC1=NN=C(c2sc3c(F)cccc3c2C)c2cc3c(cc2C1)NC(=O)C(C)O3]

(−)-6-(7-Fluoro-3-methyl-1-benzothiophen-2-yl)-3,9-dimethyl-1,10-dihydro[1,4]oxazino[3,2-h][2,3]benzodiazepin-2(3H)-one The preparation of the title compound is analogous with the method described in Example 1.

The chiral chromatographic conditions were analogous with the method described in Examples 3 and 4.

Mp: 282-285° C. $[\alpha]_D$=−21.7° (c=0.5, DMSO). IR, $^1$H NMR and $^{13}$C NMR data are identical with those described for the other enantiomer in Example 39. Elementary analysis calculated: C, 64.85; H, 4.45; F, 4.66; N, 10.31; S, 7.87. Found: C, 64.11; H, 4.62; N, 10.17; S, 7.55.

EXAMPLE 40

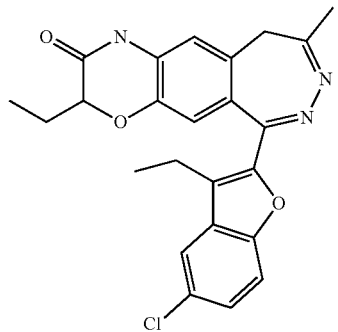 [SMILES: CCc1c(C2=NN=C(C)Cc3cc4c(cc32)OC(CC)C(=O)N4)oc2ccc(Cl)cc12]

(−)-6-(5-Chloro-3-ethyl-1-benzofuran-2-yl)-3-ethyl-9-methyl-1,10-dihydro[1,4]oxazino[3,2-h][2,3]benzodiazepin-2(3H)-one The preparation of the title compound is analogous with the method described in Example 2.

The chiral chromatographic conditions were analogous with the method described in Examples 3 and 4.

Mp: 229-231° C. $[\alpha]_D$=−39.0° (c=0.64, MeOH—CHCl$_3$ 1:1). IR (KBr, cm$^{-1}$): 2970, 1708, 1610, 1505, 1405, 1294, 1258, 1107, 1055. $^1$H NMR (DMSO-d$_6$, 400 MHz): δ 11.06 (s, 2H), 7.86 (s, 2H), 7.59 (d, 1H, J=8.6 Hz), 7.58 (d, 1H, J=8.6 Hz), 7.39 (d, 2H, J=8.7 Hz), 6.94 (s, 1H), 6.93 (s, 1H), 6.89 (s, 2H), 4.58 (dd, 1H, J=7.7, 4.5 Hz), 4.52 (dd, 1H, J=7.5, 4.3 Hz), 3.52 (d, 2H, J=12.4 Hz), 2.94 (m, 2H), 2.91 (m, 2H), 2.83 (d, 2H, J=12.4 Hz), 2.09 (s, 6H), 1.87 (m, 1H), 1.77 (m, 2H), 1.70 (m, 1H), 1.24 (t, 3H, J=7.4 Hz), 1.21 (t, 3H, J=7.4 Hz), 0.98 (t, 2H, J=7.3 Hz), 0.92 (t, 3H, J=7.3 Hz) ppm. $^{13}$C NMR (DMSO-d$_6$, 100 MHz): 166.89, 166.66, 154.73, 152.40, 149.43, 149.35, 149.11, 142.02, 141.30, 134.10, 133.92, 131.43, 131.20, 130.55, 127.60, 125.71, 125.68, 123.27, 123.15, 120.16, 120.14, 116.82, 116.76, 113.21, 113.16, 112.98, 112.93, 77.37, 77.18, 37.28, 23.58, 23.27, 22.66, 17.16, 17.11, 14.45, 14.40, 9.19, 9.15 ppm. Elementary analysis calculated: C, 66.13; H, 5.09; Cl, 8.13; N, 9.64. Found: C, 66.12; H, 5.10; Cl, 8.10; N, 9.69.

EXAMPLE 41

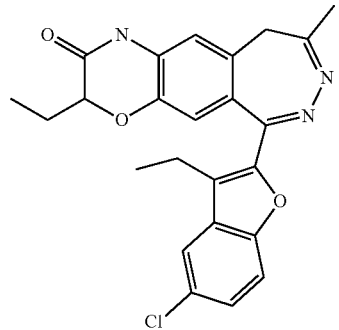 [SMILES: CCc1c(C2=NN=C(C)Cc3cc4c(cc32)OC(CC)C(=O)N4)oc2ccc(Cl)cc12]

(+)-6-(5-Chloro-3-ethyl-1-benzofuran-2-yl)-3-ethyl-9-methyl-1,10-dihydro[1,4]oxazino[3,2-h][2,3]benzodiazepin-2(3H)-one The preparation of the title compound is analogous with the method described in Example 2.

The chiral chromatographic conditions were analogous with the method described in Examples 3 and 4.

Mp: 229-231° C. $[\alpha]_D$=+32.7° (c=0.71, MeOH—CHCl$_3$ 1:1). IR, $^1$H NMR and $^{13}$C NMR data are identical with those described for the other enantiomer in Example 41. Elementary analysis calculated: C, 66.13; H, 5.09; Cl, 8.13; N, 9.64. Found: C, 66.19; H, 5.03; Cl, 8.09; N, 9.79.

EXAMPLE 42

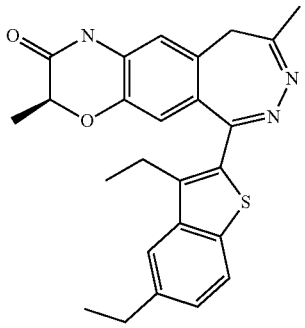 [SMILES: CCc1ccc2sc(C3=NN=C(C)Cc4cc5c(cc43)O[C@@H](C)C(=O)N5)c(CC)c2c1]

(+)-6-(3,5-Diethyl-1-benzothiophen-2-yl)-3,9-dimethyl-1,10-dihydro[1,4]oxazino[3,2-h][2,3]benzodiazepin-2(3H)-one The preparation of the title compound is analogous with the method described in Example 1.

The chiral chromatographic conditions were analogous with the method described in Examples 3 and 4.

Mp: 194-196° C. $[\alpha]_D$=+17.2° (c=0.6, MeOH—CHCl$_3$ 1:1). IR (KBr, cm$^{-1}$): 2966, 1710, 1621, 1594, 1508, 1371, 1299, 1102. $^1$H NMR (DMSO-d$_6$, 400 MHz): δ 11.07 (s, 2H), 7.87 (d, 2H, J=8.2 Hz), 7.68 (s, 1H), 7.67 (s, 1H), 7.30 (d, 2H, J=8.3 Hz), 6.95 (s, 1H), 6.94 (s, 1H), 6.83 (s, 1H), 6.82 (s, 1H), 4.70 (q, 1H, J=6.7 Hz), 4.66 (q, 1H, J=6.7 Hz), 3.54 (d, 2H, J=12.4 Hz), 2.85 (d, 1H, J=12.3 Hz), 2.84 (d, 1H, J=12.3 Hz), 2.76 (q, 4H, J=7.6 Hz), 2.68 (m, 2H), 2.64 (m, 2H), 2.08 (s, 6H), 1.39 (d, 3H, J=6.8 Hz), 1.36 (d, 3H, J=6.8 Hz), 1.26 (t, 6H, J=7.5 Hz), 1.06 (t, 3H, J=7.5 Hz), 1.02 (t, 3H, J=7.5 Hz) ppm. $^{13}$C NMR (DMSO-d$_6$, 100 MHz): 167.38, 167.19, 154.56, 152.51, 152.41, 142.10, 141.81, 140.40, 140.38, 139.98, 139.94, 138.41, 138.36, 136.99, 136.97, 135.85, 135.84, 133.75, 131.55, 131.54, 126.13, 125.02, 124.91, 122.45, 121.40, 116.76, 116.67, 113.00, 112.94, 72.92, 72.77, 37.24, 28.45, 22.70, 22.69, 20.37, 20.33, 16.28, 16.23, 16.09, 14.61, 14.48 ppm. Elementary analysis calculated: C, 69.58; H, 5.84; N, 9.74; S, 7.43. Found: C, 69.38; H, 5.84; N, 9.71; S, 7.36.

EXAMPLE 43

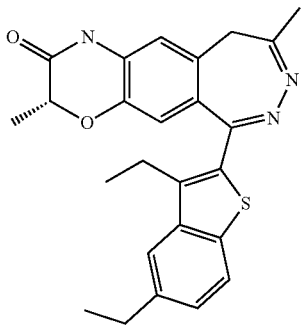 [SMILES: CCc1ccc2sc(C3=NN=C(C)Cc4cc5c(cc43)O[C@H](C)C(=O)N5)c(CC)c2c1]

(−)-6-(3,5-Diethyl-1-benzothiophen-2-yl)-3,9-dimethyl-1,10-dihydro[1,4]oxazino[3,2-h][2,3]benzodiazepin-2(3H)-one The preparation of the title compound is analogous with the method described in Example 1.

The chiral chromatographic conditions were analogous with the method described in Examples 3 and 4.

Mp: 194-196° C. $[\alpha]_D$=−23.0° (c=0.6, MeOH—CHCl$_3$ 1:1). IR, $^1$H NMR and $^{13}$C NMR data are identical with those described for the other enantiomer in Example 43. Elementary analysis calculated: C, 69.58; H, 5.84; N, 9.74; S, 7.43. Found: C, 69.39; H, 5.83; N, 9.64; S, 7.32.

EXAMPLE 44

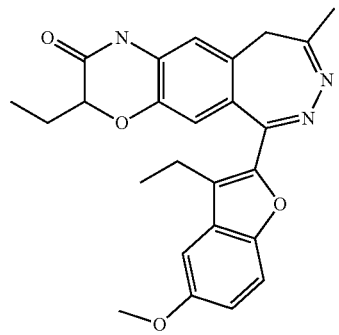 [SMILES: CCc1c(C2=NN=C(C)Cc3cc4c(cc32)OC(CC)C(=O)N4)oc2ccc(OC)cc12]

(−)-3-Ethyl-6-(3-ethyl-5-methoxy-1-benzofuran-2-yl)-9-methyl-1,10-dihydro[1,4]oxazino[3,2-h][2,3]benzodiazepin-2(3H)-one The preparation of the title compound is analogous with the method described in Example 2.

The chiral chromatographic conditions were analogous with the method described in Examples 3 and 4.

Mp: 215-217° C. $[\alpha]_D$=−35.1° (c=0.6, MeOH—CHCl$_3$ 1:1). IR (KBr, cm$^{-1}$): 2970, 1696, 1616, 1596, 1506, 1474, 1373, 1334, 1215. $^1$H NMR (DMSO-d$_6$, 400 MHz): δ 11.05 (s, 2H), 7.44 (d, 1H, J=8.9 Hz), 7.43 (d, 1H, J=8.9 Hz), 7.23 (s, 1H), 7.22 (s, 1H), 6.97 (d, 1H, J=8.9 Hz), 6.96 (d, 1H, J=8.9 Hz), 6.93 (s, 1H), 6.92 (s, 1H), 6.85 (s, 2H), 4.58 (dd, 1H, J=8.1, 4.6 Hz), 4.52 (dd, 1H, J=7.7, 4.4 Hz), 3.84 (s, 6H), 3.50 (d, 2H, J=12.4 Hz), 2.94 (m, 2H), 2.91 (m, 2H), 2.83 (d, 2H, J=12.5 Hz), 2.08 (s, 6H), 1.87 (m, 1H), 1.77 (m, 2H), 1.69 (m, 1H), 1.26 (t, 3H, J=7.5 Hz), 1.24 (t, 3H, J=7.6 Hz), 0.98 (t, 3H, J=7.3 Hz), 0.92 (t, 3H, J=7.3 Hz) ppm. $^{13}$C NMR (DMSO-d$_6$, 100 MHz): 166.92, 166.69, 155.85, 154.67, 149.40, 148.88, 148.65, 148.57, 141.95, 141.25, 134.06, 133.88, 131.30, 131.08, 129.51, 123.79, 123.47, 123.36, 116.89, 116.84, 114.75, 114.71, 112.93, 112.88, 112.18, 112.12, 102.64, 102.62, 77.38, 77.18, 55.88, 37.26, 23.58, 23.28, 22.68, 17.32, 17.27, 14.50, 14.46, 9.22, 9.17 ppm. Elementary analysis calculated: C, 69.59; H, 5.84; N, 9.74. Found: C, 69.65; H, 5.97; N, 9.87.

EXAMPLE 45

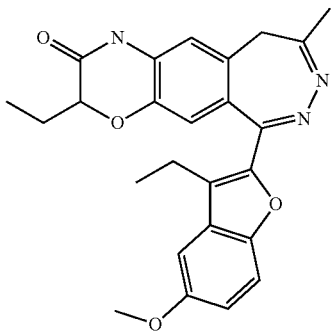 [SMILES: CCc1c(C2=NN=C(C)Cc3cc4c(cc32)OC(CC)C(=O)N4)oc2ccc(OC)cc12]

(+)-3-Ethyl-6-(3-ethyl-5-methoxy-1-benzofuran-2-yl)-9-methyl-1,10-dihydro[1,4]oxazino[3,2-h][2,3]benzodiazepin-2(3H)-one The preparation of the title compound is analogous with the method described in Example 2.

The chiral chromatographic conditions were analogous with the method described in Examples 3 and 4.

Mp: 215-217° C. $[\alpha]_D$=+31.7° (c=0.56, MeOH—CHCl$_3$ 1:1). IR, $^1$H NMR and $^{13}$C NMR data are identical with those described for the other enantiomer in Example 45. Elementary analysis calculated: C, 69.59; H, 5.84; N, 9.74. Found: C, 69.47; H, 5.88; N, 9.67.

EXAMPLE 46

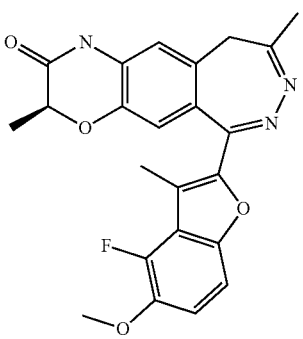 [SMILES: COc1ccc2oc(C3=NN=C(C)Cc4cc5c(cc43)O[C@@H](C)C(=O)N5)c(C)c2c1F]

(+)-6-(4-Fluoro-5-methoxy-3-methyl-1-benzofuran-2-yl)-3,9-dimethyl-1,10-dihydro[1,4]oxazino[3,2-h][2,3]benzodiazepin-2(3H)-one The preparation of the title compound is analogous with the method described in Example 2.

The chiral chromatographic conditions were analogous with the method described in Examples 3 and 4.

Mp: 237-238° C. $[\alpha]_D$=+33.9° (c=0.8, MeOH—CHCl$_3$ 1:1). IR (KBr, cm$^{-1}$): 2936, 1705, 1619, 1510, 1437, 1377, 1326, 1257, 1043. $^1$H NMR (DMSO-d$_6$, 400 MHz): δ 11.06 (s, 2H), 7.34 (d, 2H, J=8.9 Hz), 7.24 (t, 2H, J=8.6 Hz), 6.94 (s, 1H), 6.93 (s, 1H), 6.92 (s, 1H), 6.90 (s, 1H), 4.76 (q, 1H, J=6.8 Hz), 4.68 (q, 1H, J=6.8 Hz), 3.88 (s, 6H), 3.52 (d, 1H, J=12.4 Hz), 3.51 (d, 1H, J=12.4 Hz), 2.83 (d, 1H, J=12.2 Hz), 2.82 (d, 1H, J=12.3 Hz), 2.50 (s, 3H), 2.46 (s, 3H), 2.08 (s, 6H), 1.43 (d, 3H, J=6.7 Hz), 1.38 (d, 3H, J=6.8 Hz) ppm. $^{13}$C NMR (DMSO-d$_6$, 100 MHz): 167.48, 167.25, 154.82, 154.79, 149.27 (d, J=8.1 Hz), 149.10 (d, J=1.5 Hz), 149.05, 148.99, 148.97 (d, J=1.5 Hz), 145.44 (d, J=248.7 Hz), 142.56, 142.37, 141.89, 134.25, 134.09, 131.59, 123.13, 112.98, 119.43 (d, J=16.1 Hz), 119.42 (d, J=16.2 Hz), 116.83, 116.77, 115.55 (d, J=3.2 Hz), 115.52 (d, J=3.1 Hz), 113.73 (d, J=2.8 Hz), 113.07, 112.99, 107.21 (d, J=4.5 Hz), 72.89, 72.78, 57.67, 37.25, 22.71, 22.70, 16.35, 16.03, 10.97 (d, J=2.2 Hz), 10.95 (d, J=2.2 Hz) ppm. Elementary analysis calculated: C, 65.55; H, 4.78; F, 4.51; N, 9.97. Found: C, 65.67; H, 4.74; N, 9.95.

EXAMPLE 47

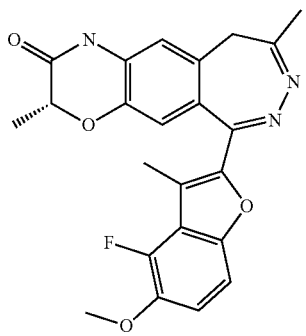 [SMILES: COc1ccc2oc(C3=NN=C(C)Cc4cc5c(cc43)O[C@H](C)C(=O)N5)c(C)c2c1F]

(−)-6-(4-Fluoro-5-methoxy-3-methyl-1-benzofuran-2-yl)-3,9-dimethyl-1,10-dihydro[1,4]oxazino[3,2-h][2,3]benzodiazepin-2(3H)-one The preparation of the title compound is analogous with the method described in Example 2.

The chiral chromatographic conditions were analogous with the method described in Examples 3 and 4.

Mp: 237-238° C. $[\alpha]_D$=−37.4° (c=0.75, MeOH—CHCl$_3$ 1:1). IR, $^1$H NMR and $^{13}$C NMR data are identical with those described for the other enantiomer in Example 47. Elementary analysis calculated: C, 65.55; H, 4.78; F, 4.51; N, 9.97. Found: C, 65.41; H, 4.73; N, 9.93.

EXAMPLE 48

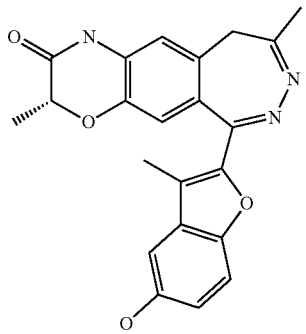 [SMILES: CC1=NN=C(c2oc3ccc(O)cc3c2C)c2cc3c(cc2C1)NC(=O)[C@@H](C)O3]

(−)-6-(5-Hydroxy-3-methyl-1-benzofuran-2-yl)-3,9-dimethyl-1,10-dihydro[1,4]oxazino[3,2-h][2,3]benzodiazepin-2(3H)-one The preparation of the title compound is analogous with the method described in Example 2.
The chiral chromatographic conditions were analogous with the method described in Examples 3 and 4.
Mp: 285-289° C. [α]$_D$=−32.3° (c=1, MeOH—CHCl$_3$ 1:1). IR (KBr, cm$^{-1}$): 3378, 3200, 1690, 1665, 1189. $^1$H NMR (DMSO-d$_6$, 500 MHz): δ 11.00 (br s, 1H), 9.26 (br s, 1H), 7.32 (d, J=8.6 Hz, 1H), 6.95 (d, 1H), 6.94-6.93 (s, 1H), 6.87-6.85 (s, 1H), 6.82 (dd, J=2.0, 8.6 Hz, 1H), 4.77-4.68 (q, J=7.0 Hz, 1H), 3.48 (d, J=12.5 Hz, 1H), 2.81 (d, J=12.3 Hz, 1H), 2.33-2.30 (s, 3H), 2.07 (s, 3H), 1.43-1.38 (d, J=6.8 Hz, 3H) ppm. $^{13}$C NMR (DMSO-d$_6$, 125 MHz): 167.42, 167.20, 154.56, 154.53, 153.53, 149.48, 149.45, 148.67, 148.53, 147.99, 147.97, 142.22, 141.76, 134.16, 134.00, 131.35, 130.65, 123.25, 123.11, 117.24, 117.20, 116.83, 114.92, 112.95, 112.86, 111.71, 104.38, 72.87, 72.77, 37.19, 22.65, 16.33, 16.02, 9.68 ppm. Elementary analysis calculated: C, 67.86; H, 4.92; N, 10.79. Found: C, 67.08; H, 5.00; N, 10.32.

EXAMPLE 49

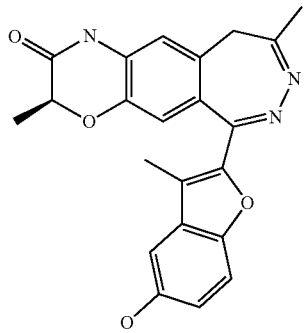 [SMILES: CC1=NN=C(c2oc3ccc(O)cc3c2C)c2cc3c(cc2C1)NC(=O)[C@H](C)O3]

(+)-6-(5-Hydroxy-3-methyl-1-benzofuran-2-yl)-3,9-dimethyl-1,10-dihydro[1,4]oxazino[3,2-h][2,3]benzodiazepin-2(3H)-one The preparation of the title compound is analogous with the method described in Example 2.
The chiral chromatographic conditions were analogous with the method described in Examples 3 and 4.
Mp: 263-288° C. [α]$_D$=+30.2° (c=1, MeOH—CHCl$_3$ 1:1). IR, $^1$H NMR and $^{13}$C NMR data are identical with those described for the other enantiomer in Example 49. Elementary analysis calculated: C, 67.86; H, 4.92; N, 10.79. Found: C, 66.99; H, 4.98; N, 10.36.

EXAMPLE 50

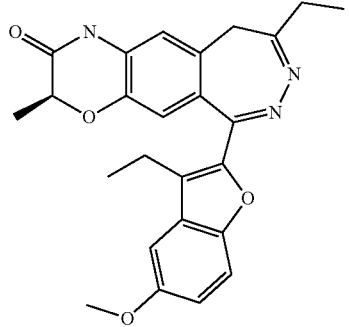 [SMILES: CCC1=NN=C(c2oc3ccc(OC)cc3c2CC)c2cc3c(cc2C1)NC(=O)[C@H](C)O3]

(+)-9-Ethyl-6-(3-ethyl-5-methoxy-1-benzofuran-2-yl)-3-methyl-1,10-dihydro[1,4]oxazino[3,2-h][2,3]benzodiazepin-2(3H)-one The preparation of the title compound is analogous with the method described in Example 2.
The chiral chromatographic conditions were analogous with the method described in Examples 3 and 4.
Mp: 226-228° C. [α]$_D$=+30.4° (c=1, MeOH—CHCl$_3$ 1:1). IR (KBr, cm$^{-1}$): 3071, 1705, 1509, 1481, 1212. $^1$H NMR (DMSO-d$_6$, 400 MHz): δ 11.03 (br s, 1H), 7.43 (d, J=8.9 Hz, 1H), 7.22 (d, 1H), 6.95 (dd, J 1=2.3 Hz, J 2=8.9 Hz, 1H), 6.92 (s, 1H), 6.82-6.80 (s, 1H), 4.76-4.67 (q, J=6.8 Hz, 1H), 3.55 (d, J=12.5 Hz, 1H), 2.95 (m, 2H), 2.80 (d, J=12.4 Hz, 1H), 2.44 (m, 1H), 2.36 (m, 1H), 1.42-1.37 (d, J=6.7 Hz, 3H), 1.24 (t, J=7.4 Hz, 3H), 1.07 (t, J=7.4 Hz, 3H) ppm. $^{13}$C NMR (DMSO-d$_6$, 100 MHz): 167.44, 167.22, 158.70, 155.85, 149.35, 148.88, 148.57, 142.11, 141.73, 134.46, 134.37, 131.43, 129.51, 123.73, 123.30, 116.72, 114.69, 112.19, 102.65, 72.88, 72.78, 55.89, 36.32, 29.57, 29.52, 16.34, 16.09, 14.59, 14.53, 10.67, 10.61 ppm. Elementary analysis calculated: C, 69.59; H, 5.84; N, 9.74. Found: C, 68.87; H, 5.94; N, 9.67.

EXAMPLE 51

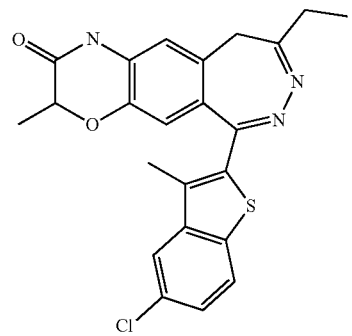 [SMILES: CCC1=NN=C(c2sc3ccc(Cl)cc3c2C)c2cc3c(cc2C1)NC(=O)C(C)O3]

(−)-6-(5-Chloro-3-methyl-1-benzothiophen-2-yl)-9-ethyl-3-methyl-1,10-dihydro[1,4]oxazino[3,2-h][2,3]benzodiazepin-2(3H)-one The preparation of the title compound is analogous with the method described in Example 1.
The chiral chromatographic conditions were analogous with the method described in Examples 3 and 4.
Mp: 270-272° C. [α]$_D$=−19.0° (c=1, MeOH—CHCl$_3$ 1:1). IR (KBr, cm$^{-1}$): 3050, 1705, 1505, 1310, 1080. $^1$H NMR (DMSO-d$_6$, 500 MHz): δ 11.04 (br s, 1H), 8.03 (d, J=8.6 Hz, 1H), 7.89-7.87 (d, J=2.0 Hz, 1H), 7.46 (dd, J$_1$=2.0 Hz, J$_2$=8.6 Hz, 1H), 6.96-6.95 (s, 1H), 6.84-6.82 (s, 1H), 4.72-4.68 (q, J=6.8 Hz, 1H), 3.58 (d, J=12.5 Hz, 1H), 2.83 (d, J=12.5 Hz, 1H), 2.49 (m, 1H), 2.38 (m, 1H), 2.04-1.99 (s, 3H), 1.40-1.37 (d, J=6.8 Hz, 3H), 1.07 (t, J=7.4 Hz, 3H) ppm. $^{13}$C NMR (DMSO-d$_6$, 125 MHz): 167.41, 167.17, 158.75, 158.73, 152.33, 152.24, 142.31, 142.25, 142.18, 142.13, 138.44, 138.42, 137.48, 137.46, 134.11, 134.03, 131.94, 131.65, 131.60, 129.76, 129.73, 125.67, 124.47, 124.29, 124.22, 122.20, 116.63, 116.58, 113.15, 113.07, 72.91, 72.75, 36.30, 29.58, 29.54, 16.26, 15.97, 13.73, 13.67, 10.59, 10.53 ppm. Elementary analysis calculated: C, 63.08; H, 4.60; Cl, 8.10; N, 9.59; S, 7.32. Found: C, 62.88; H, 4.52; Cl, 8.13; N, 9.48; S, 7.22.

EXAMPLE 52

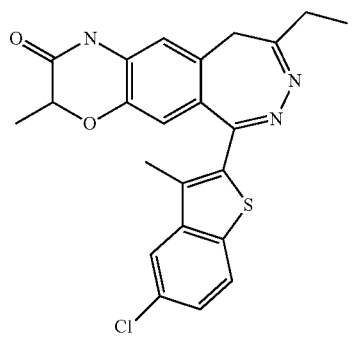 [SMILES: CCC1=NN=C(c2sc3ccc(Cl)cc3c2C)c2cc3c(cc2C1)NC(=O)C(C)O3]

(+)-6-(5-Chloro-3-methyl-1-benzothiophen-2-yl)-9-ethyl-3-methyl-1,10-dihydro[1,4]oxazino[3,2-h][2,3]benzodiazepin-2(3H)-one The preparation of the title compound is analogous with the method described in Example 1.

The chiral chromatographic conditions were analogous with the method described in Examples 3 and 4.

Mp: 271-273° C. $[\alpha]_D=+19.0°$ (c=1, MeOH—CHCl$_3$ 1:1). IR, $^1$H NMR and $^{13}$C NMR data are identical with those described for the other enantiomer in Example 52. Elementary analysis calculated: C, 63.08; H, 4.60; Cl, 8.10; N, 9.59; S, 7.32. Found: C, 62.85; H, 4.57; Cl, 8.24; N, 9.53; S, 7.30.

Pharmacological Studies

Effect on GABA$_A$ $\alpha_1$, $\alpha_2$ and $\alpha_5$ subunits.

Method

The compounds are tested on HEK-293 (Human Embryonic Kidney) cells stably expressing the $\alpha_2$ $\alpha_2$ or the $\alpha_5$ subunit of the human GABA$_A$ receptor in association with the beta2 (short) and gamma2 (long) subunits, thus forming heteropentameric GABA$_A$ receptors. The cells are maintained in the presence of a selection of three antibiotics—neomycin, zeocin and puromycin—in a Dulbecco medium (DMEM) containing 10% (v/v) foetal bovine serum The membrane potential is monitored using the fluorescent blue FMP dye (Molecular Devices), following the instructions of the manufacturer. On the day before the experiment, the cells are transferred to 96-well plates (in a density of 50,000 cells/well). 18-24 h later the cells are washed and incubated with the compounds under test plus the FMP dye. Recording of the fluorescence signal in a FlexStation3 plate reader (Molecular Devices, USA) is started 40 min later. After 30 sec of monitoring baseline fluorescence GABA is added to evoke a fluorescent signal reporting depolarisation of the membrane potential across the plasma membrane. The GABA induced responses are recorded for 90 seconds. Data are calculated by subtracting the average baseline value and computing the area under the curve of the fluorescence signal induced by GABA. The IC$_{50}$ values for $\alpha_5$ and the EC50 values for $\alpha_2$ of the tested compounds are determined from log concentration versus response curves obtained by non-linear regression using SoftMax Pro software (Molecular Devices, USA).

TABLE 1

Effects of experimental compounds conforming to formula I on GABA responses in HEK 293 cells expressing various types of GABA$_A$ receptors.

| Example | $\alpha_1$ IC$_{50}$ µmol/L | $\alpha_2$ EC$_{50}$ µmol/L | $\alpha_5$ IC$_{50}$ µmol/L |
|---|---|---|---|
| 1 | >10 | 3.5 | 0.7 |
| 12 | >10 | 1 | 3 |
| 5 | >10 | 1.2 | 0.9 |
| 8 | >10 | 1 | 3 |
| 2 | >10 | 0.8 | 0.8 |
| 9 | >10 | 1 | 0.7 |
| 13 | >10 | 1.1 | 1.3 |
| 14 | 13.7 | 1 | 0.43 |

$\alpha_1$ and $\alpha_5$ expressed as % of GABA EC$_{50}$.
$\alpha_2$ expressed as % of the maximal effect of 100 nmol/L TPA-023 ran as internal standard at GABA EC$_{20}$ On the basis of results shown in Table 1 the compounds of formula (I) of the present invention markedly enhance the GABA response in cells expressing GABA$_A$ $\alpha_2$ subunits, whilst inhibiting the effect of GABA in cells expressing $\alpha_5$ subunits, and having a weak or negligible effect on α1 containing GABA$_A$ receptors. The effect is considered weak if the EC$_{50}$/IC$_{50}$ value is >10 µmol/L.

Pharmacological Activity

Procognitive Efficacy

Methods

Novel Object Recognition Test in Mice

Figure 2:
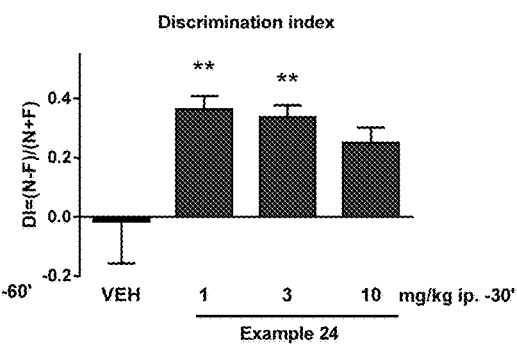

The novel object recognition test evaluates the ability of mice to detect novelty in an otherwise familiar environment. Subsequent a short exploratory period, mice are unable to discriminate between the familiar and the new object 24 hours later. Administration of pro-cognitive agents—before the short exploratory session—can significantly increase the time spent exploring the novel object on the following (retention) day. Enhancement of the discrimination index is considered as a procognitive effect. The results are illustrated in FIG. 1 and FIG. 2.

Radial Maze Test in Rats

Figure 3:
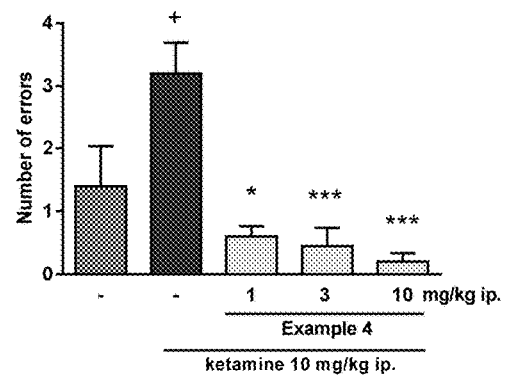
FIG. 3. Reduction of the ketamine-induced deficit in working memory after ip. Administration of the compound of Example 4, in rats Mean values±S.E.M. (n=9-10); Mann-Whitney U test (# $p<0.05$, control vs. control treated with carrier); Dunn test after Kruskal-Wallis ANOVA (* $p<0.05$, $p<0.01$, *$p<0.001$ vs. control treated with ketamine).

The 8-arm maze working memory test evaluates short-term memory in rats. After about 15 days of learning trials the animals can acquire the ability to visit each arm only once. NMDA antagonist agents (for example ketamine, phencyclidine) disrupt this ability—the animals make more errors i.e. visit arms more than once. Administration of pro-cognitive agents before the trial significantly improves diminished performance in this test. The results are illustrated in FIG. 3. The results show that the compounds of the invention bring about a significant improvement of memory function in laboratory animals.

Antipsychotic Activity

Method

Prepulse Inhibition Test in Mice

Figure 4:
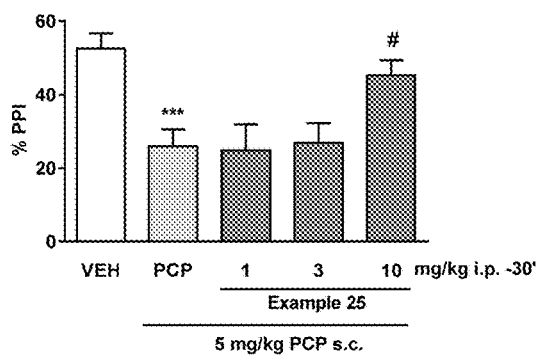
FIG. 4. Ameliorating effect of the compound of Example 25 in the PCP-induced PPI disruption model in mice after i.p. administration. Mean values±S.E.M. (n=10-12/group) Student's t-test: vehicle vs. PCP-treated group (***$p<0.001$) Dunnett's test following ANOVA: PCP-treated vs. PCP+ compound treated groups (#:$p<0.05$).

The startle reaction of a healthy rodents and humans to a strong acoustic stimulus is reduced by the prior presentation of a weak stimulus. The effect of the weak stimulus on the startle response has been termed prepulse inhibition (PPI). Reduced prepulse inhibition is a hallmark feature of attention-processing (sensorimotor gating) deficits in patients with schizophrenia and other psychotic disorders. Acute administration of phencyclidine (PCP), an antagonist of N-methyl D-aspartate (NMDA)-type glutamate receptors, disrupts PPI in rodents and this effect can be prevented by clinically effective antipsychotics. The results are illustrated in FIG. 4. The results show that the compounds of the invention exert antipsychotic activity.

Anxiolytic Activity
Methods
Light-Dark Test in Mice

Figure 5:
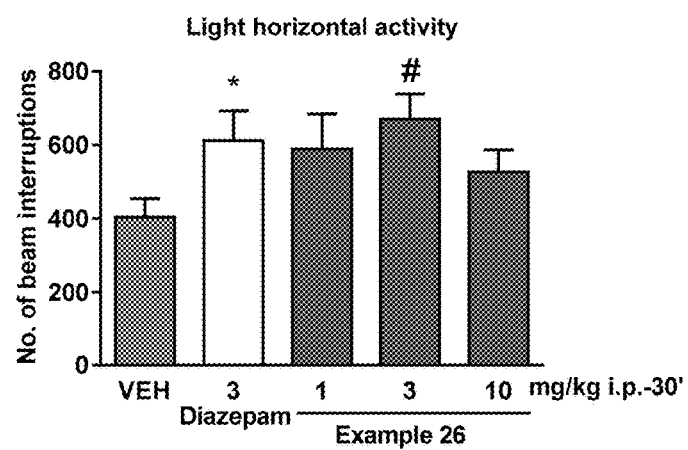
FIG. 5. Anxiolytic activity of the compound of Example 26 in Light-dark test in mice after i.p. administration (Increased activity in the light compartment). Mean values±S.E.M. (n=11-20/group) Student's t-test: vehicle vs. Diazepam-treated group (*$p<0.05$) Dunnett test following ANOVA: vehicle-treated vs. compound-treated groups (#:$p<0.05$).

The light-dark apparatus contains a light (brightly illuminated) and a dark compartment. A small opening connects the two parts. During the 5 minutes test mice were placed individually in the light compartment and allowed to explore the entire apparatus. The activity of animals was measured automatically by interruptions of horizontal and vertical infrared beams. An increase of time spent in the light area (increase in light horizontal time) is interpreted as an anxiolytic effect. The results are illustrated in FIG. 5.

Social Interaction Test in Rats

Figure 6:
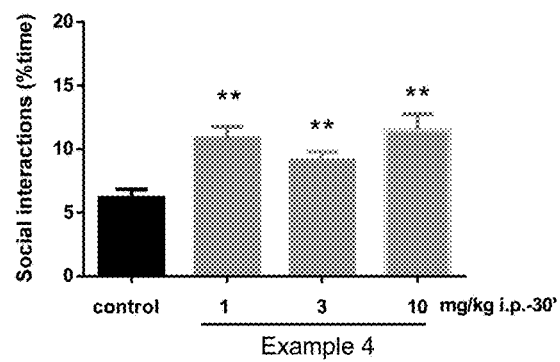
FIG. 6. Anxiolytic activity of the compound of Example 4 in the social interaction model in rats after i.p. administration. Mean values±S.E.M. (n=12/group) Kruskal-Wallis ANOVA followed by Mann-Whitney U test: control vs. compound-treated groups (**:$p<0.05$).

The social interaction test is a model used to measure anxiolytic or anxiogenic behaviour in rodents. When a pair of unfamiliar rats is placed together in the open field the animals show specific social behaviours (sniffing, following, grooming, crawling over and under other rats). Anxiolytic compounds such as benzodiazepines increase in the time spent with social interactions. In our experiment rats were submitted to the social interaction test of anxiety 30 min after drug treatment. The social interaction test consisted of 10 min of social encounters between two animals that received the same pharmacological treatment. The results are illustrated in FIG. 6. The results show that the compounds of invention demonstrate significant anxiolytic efficacy.

The invention claimed is:

1. A compound of formula (I)

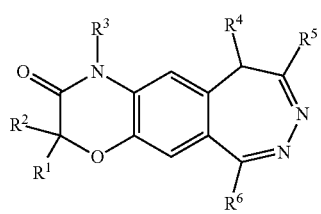

(I)

wherein
$R^1$, $R^2$ are independently hydrogen or $C_{1-4}$ alkyl;
$R^3$ is hydrogen or a $C_{1-4}$ alkyl group which is unsubstituted or substituted by phenyl, pyridyl, or amino optionally substituted by $C_{1-4}$ alkyl;
$R^4$ is hydrogen;
$R^5$ is a $C_{1-4}$ alkyl group;
$R^6$ is a
  monocyclic aryl, which is a six membered ring unsubstituted or substituted by one or more identical or different groups selected from the group consisting of $C_{1-4}$ alkyl groups, $C_{1-4}$ alkoxy, halogenated $C_{1-4}$ alkyl, phenyl, phenoxy, halogen, and nitro; or
  mono- or bi- or tricyclic heteroaryl group consisting of five or six membered ring(s) having 1 to 3 identical or different hetero atoms selected from the group consisting of nitrogen, oxygen and sulfur, in which at least one of the rings is aromatic, and wherein the rings are optionally substituted by one or more identical or different groups selected from the group consisting of $C_{1-4}$ alkyl, mono-, di-, tri-halogenated $C_{1-4}$ alkyl, $C_{1-4}$ alkoxy, hydroxyl, and halogen;
or a salt thereof with a pharmaceutically acceptable acid or a solvate thereof.

2. The compound of formula (I) according to claim 1, wherein
$R^1$, $R^2$ is propyl, ethyl, methyl or hydrogen,
$R^3$ is hydrogen, methyl, ethyl, or benzyl and
$R^5$ is methyl or ethyl.

3. The compound of formula (I) according to claim 1, wherein
$R^1$, $R^2$ is methyl or hydrogen,
$R^3$ is hydrogen and $R^5$ is methyl.

4. The compound according to claim 1, wherein
$R^6$ is phenyl substituted by one or more halogen or $C_{1-4}$ alkyl which is substituted by one or more halogen.

5. The compound according to claim 4, wherein
$R^6$ is phenyl substituted by one or more fluoro or trifluoromethyl.

6. The compound of formula (I) according to claim 1, wherein
$R^6$ is a benzofuranyl or a benzothienyl group wherein the rings are optionally substituted by one or more identical or different groups selected from the group consisting of $C_{1-4}$ alkyl, $C_{1-4}$ haloalkyl, $C_{1-4}$ alkoxy, halogen, and hydroxyl.

7. The compound of formula (I) according to claim 1, wherein
$R^1$, $R^2$ is propyl, ethyl, methyl or hydrogen, and
$R^3$ is hydrogen, methyl, ethyl or benzyl,
$R^5$ is methyl or ethyl, and
$R^6$ is a 1-benzofuran-2-yl or 1-benzothiophen-2-yl group which is substituted by one to three identical or different groups which are independently selected from the group consisting of $C_{1-4}$ alkyl, $C_{1-4}$ alkoxy, halogen, and hydroxyl.

8. The compound of formula (I) according to claim 6, wherein
$R^6$ is a 1-benzofuran-2-yl or 1-benzothiophen-2-yl group which is substituted by one to three identical or different groups which are independently selected from the group consisting of methyl, ethyl, methoxy, fluoro, chloro and hydroxyl.

9. The compound of formula (I) according to claim 8, wherein
$R^6$ is a 1-benzofuran-2-yl group, substituted in position 3 by ethyl or methyl and in any of positions 4 to 7 by one or two identical or different group(s) independently selected from the group consisting of ethyl, chloro, methoxy, and hydroxyl.

10. The compound of formula (I) according to claim 8, wherein
$R^6$ represents a 1-benzothiophen-2-yl group substituted in position 3 by ethyl or methyl and in any of positions 4 to 7 by one or two identical or different group(s) independently selected from the group consisting of chloro and fluoro.

11. The compound of formula (I) according to claim 6, wherein
$R^1$, $R^2$ is methyl or hydrogen,
$R^3$, $R^4$ is hydrogen,
$R^5$ is methyl, and
$R^6$ is a 1-benzofuran-2-yl or 1-benzothiophen-2-yl group which is substituted by one to three identical or different groups which are independently selected from the group consisting of methyl, ethyl, methoxy, fluoro, chloro, and hydroxyl.

12. The compound of formula (I) according to claim 11, wherein
$R^1$, $R^2$ is methyl or hydrogen,
$R^4$, $R^3$ is hydrogen,
$R^5$ is methyl and R⁶ represents a 1-benzofuran-2-yl group, substituted in position 3 by ethyl or methyl and in any of positions 4 to 7 by one or two identical or different group(s) independently selected from the group consisting of ethyl, chloro, methoxy, and hydroxyl.

13. The compound of formula (I) according to claim 11, wherein
R¹, R² is methyl or hydrogen,
R⁴, R³ is hydrogen,
R⁵ is methyl and
R⁶ represents a 1-benzothien-2-yl group, substituted in position 3 by ethyl or methyl and in any of positions 4 to 7 by one or two identical or different group(s) independently selected from the group consisting of chloro, and fluoro.

14. A compound, which is
6-(4-fluoro-3-methyl-1-benzothiophen-2-yl)-3,9-dimethyl-1,10-dihydro[1,4]oxazino-[3,2-h][2,3]benzodiazepin-2(3H)-one;
6-(5-methoxy-3-methyl-1-benzofuran-2-yl)-3,9-dimethyl-1,10-dihydro[1,4]oxazino[3,2-h][2,3]benzodiazepin-2(3H)-one;
6-(6-chloro-3-methyl-1-benzothiophen-2-yl)-3,9-dimethyl-1,10-dihydro[1,4]oxazino[3,2-h][2,3]benzodiazepin-2(3H)-one;
6-(6-chloro-5-fluoro-3-methyl-1-benzothiophen-2-yl)-3,9-dimethyl-1,10-dihydro[1,4]oxazino[3,2-h][2,3]benzodiazepin-2(3H)-one;
6-(5-chloro-3-ethyl-1-benzothiophen-2-yl)-3,9-dimethyl-1,10-dihydro[1,4]oxazino[3,2-h][2,3]benzodiazepin-2(3H)-one;
6-(5-chloro-3-methyl-1-benzofuran-2-yl)-3,9-dimethyl-1,10-dihydro[1,4]oxazino[3,2-h][2,3]benzodiazepin-2(3H)-one;
6-(3,5-diethyl-1-benzofuran-2-yl)-3,9-dimethyl-1,10-dihydro[1,4]oxazino[3,2-h][2,3]benzodiazepin-2(3H)-one; or
6-(5-hydroxy-3-methyl-1-benzofuran-2-yl)-3,9-dimethyl-1,10-dihydro[1,4]oxazino[3,2-h][2,3]benzodiazepin-2(3H)-one.

15. A process for preparing a compound of formula (I) according to claim 1, comprising treating a compound of formula (II)

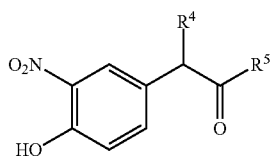
(II)

wherein
R⁴ is hydrogen and
R⁵ represents a linear or branched $C_{1-4}$ alkyl group;
with a compound of formula (III)

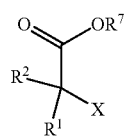
(III)

wherein
R¹ and R² are independently hydrogen or a linear or branched $C_{1-4}$ alkyl;
R⁷ represents linear or branched $C_{1-4}$ alkyl group,
X represents a leaving group,
to yield a compound of formula (IV)

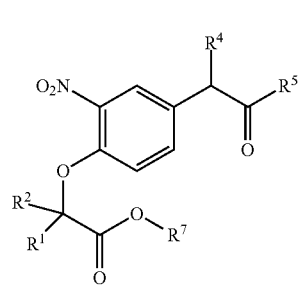
(IV)

which is reduced and optionally N-alkylated to yield a compound of formula (V),

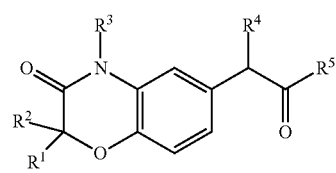
(V)

wherein
R¹, R², R³, R⁴ and R⁵ are as defined for formula (I);
brominating the compound of formula (V) to give a compound of formula (VI),

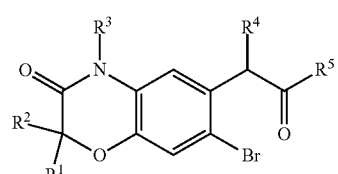
(VI)

converting the compound of formula (VI) by treatment with at least one alcohol or diol into a compound of formula (VII)

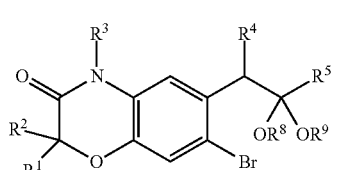
(VII)

wherein
R¹, R², R³, R⁴ and R⁵ are as defined for formula (I), and
R⁸ and R⁹ each represents a $C_{1-4}$ alkyl group, or
R⁸ and R⁹ together form $C_{2-6}$ alkylene;
converting the thus obtained product by exchanging the bromo atom for an alkali or magnesium atom and reacting the thus-obtained alkali or magnesium compound with an approximately equimolar amount of a carboxylic acid compound of formula (VIII) to give a compound of formula (IX)

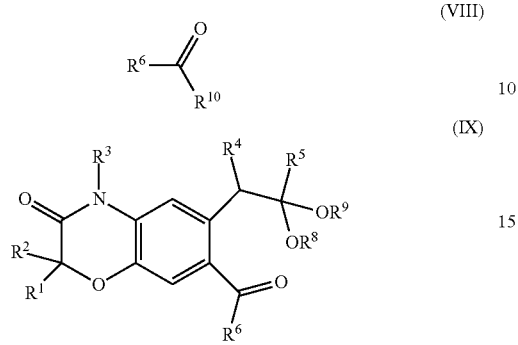

wherein
$R^1$, $R^2$, $R^3$,
$R^4$, $R^4$ and $R^6$ are as defined for formula (I),
$R^8$ and $R^9$ each represents a $C_{1-4}$ alkyl group, or
$R^8$ and $R^9$ together form $C_{2-6}$ alkylene,
$R^{10}$ represents Cl, or Br, or $OR^{11}$, or $NR^{12}R^{13}$,
$R^{11}$ represents $C_{1-4}$ alkyl,
$R^{12}$ and $R^{13}$ each denotes a $C_{1-4}$ alkyl or a methoxy group;
and transforming the compound of formula (IX) into the compound of formula (I).

16. A method for transforming a compound of formula (IX) into a compound of formula (I) according to claim 1, comprising
a) treating the compound of formula (IX) with an acid followed by cyclisation with hydrazine or hydrazine hydrate to produce the compound of formula (I), or

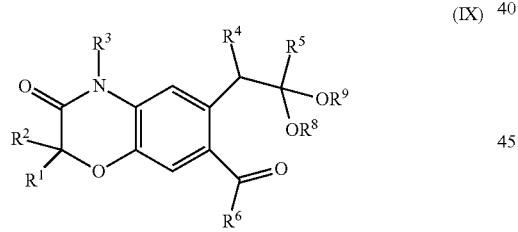

b) converting the compound of formula (IX) by acidic treatment into the compound (X)

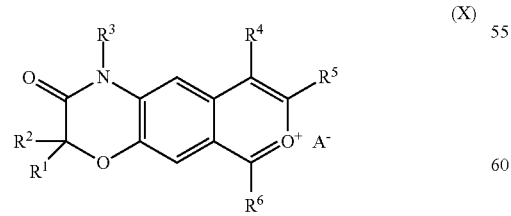

wherein
$R^1$, $R^2$, $R^3$, $R^4$, $R^4$ and $R^6$ are as defined for formula (I) and
$A^-$ is an anion;

and reacting the thus obtained compound of formula (X) with hydrazine or hydrazine hydrate to produce the compound of formula (I), or
c) converting the compound of formula (IX) by acidic treatment into the compound of formula (XI)

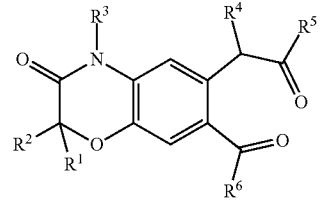

wherein
$R^1$, $R^2$, $R^3$, $R^4$, $R^5$ and $R^6$ are as defined for formula (I);
and reacting the compound of formula (XI) with hydrazine or hydrazine hydrate to produce the compound of formula (I).

17. A process for preparing a compound of formula (I) according to claim 1, comprising reducing a compound of formula (V) into an alcohol of formula (XII)

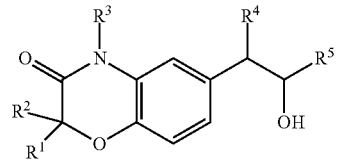

wherein
$R^1$, $R^2$, $R^3$, $R^4$ and $R^5$ are as defined for formula (I);
reacting the thus obtained product with an aldehyde of formula (XIII) under acidic conditions to afford an isochroman of formula (XIV)

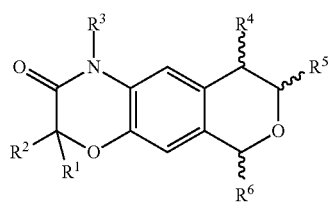

wherein
$R^6$ is as defined for formula (I);
oxidizing the compound of formula (XIV) yielding a 2-benzpyrylium salt of formula (X), or a diketone of formula (XI);

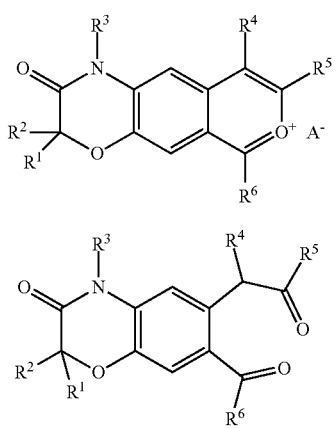

treating the compound of formula (XIV) with hydrazine or hydrazine hydrate to produce the compound of formula (I).

18. A pharmaceutical composition, comprising one or more compounds of formula (I) according to claim 1 and one or more pharmaceutically acceptable carriers.

19. A method for treating schizophrenia, unipolar depression, Alzheimer's disease, vascular dementia, Down's syndrome, fragile X syndrome, Parkinson's disease, Huntington's disease, generalised anxiety, panic disorder with or without agoraphobia, obsessive-compulsive disorder, post-traumatic stress disorder, bipolar disorder, autism spectrum disorder, sequelae of a cerebral vascular accident, sequelae of brain trauma, comprising administering a therapeutically effective amount of at least one compound of formula (I) according to claim 1 to a patient in need of such treatment.

20. The compound of claim 1, or a pharmaceutically acceptable salt thereof.

* * * * *